US005677750A

United States Patent [19]

Qi

[11] Patent Number: 5,677,750
[45] Date of Patent: Oct. 14, 1997

[54] APPARATUS FOR AND METHOD OF SIMULATING OCULAR OPTICAL SYSTEM

[75] Inventor: Hua Qi, Tokyo, Japan

[73] Assignee: Hoya Corporation, Tokyo, Japan

[21] Appl. No.: 623,560

[22] Filed: Mar. 28, 1996

[30] Foreign Application Priority Data

| Mar. 29, 1995 | [JP] | Japan | 7-071502 |
| Mar. 29, 1995 | [JP] | Japan | 7-071503 |
| Mar. 31, 1995 | [JP] | Japan | 7-076585 |
| Apr. 13, 1995 | [JP] | Japan | 7-087854 |

[51] Int. Cl.$^6$ ............................... A61B 3/10; A61B 3/14
[52] U.S. Cl. ........................... 351/205; 351/206; 351/246
[58] Field of Search .............................. 351/200, 205, 351/206, 246

[56] References Cited

U.S. PATENT DOCUMENTS 5,546,142  8/1996  Kobayashi ..................... 351/246 X

OTHER PUBLICATIONS

Hua Qi et al., "Simulation of Image Generated by Optical System of the Human Eye", Japanese Journal of Visual Science, vol. 15. No. 3, 1994.

Primary Examiner—Huy Mai
Attorney, Agent, or Firm—Armstrong, Westerman, Hattori, McLeland, & Naughton

[57] ABSTRACT

An apparatus for simulating an ocular optical system simulates a retinal image produced by a human eye through an optical lens. Optical system data are produced from an optical system including a cornea, a pupil, an intraocular lens, a retina, etc. Based on the optical system data, point spread functions each indicative of a distribution on an image plane of light emitted from a certain point are calculated by PSF (Point Spread Function) calculating means. Image data are subjected to convolutional integration with the point spread functions, determining retinal image data. The retinal image data are converted into display data, which are supplied to a display unit to display a retinal image thereon. The retinal image displayed on the display unit is an image that would be actually formed on the retina of the human eye, and provides an accurate objective indication of how the image is seen by the patient.

25 Claims, 23 Drawing Sheets

APPARATUS FOR AND METHOD OF SIMULATING OCULAR OPTICAL SYSTEM

BACKGROUND OF THE INVENTION

1. Field of the Invention

The present invention relates to an apparatus for and a method of simulating an ocular optical system, and more particularly to an apparatus for and a method of simulating a retinal image which would be viewed by a human eye that is combined with an optical lens such as an intraocular lens, an eyeglass lens, a contact lens, or the like.

2. Description of the Related Art

Optical lenses including intraocular lenses, eyeglass lenses, contact lenses, etc. are widely used for human eyes to keep normal vision. One simple way of determining an optical lens that is most suitable to correct defects of vision of a human eye is for the patient to wear an optical lens in order to achieve a subjective evaluation of corrected vision. Other objective methods that are available in the art are less practically useful.

The optical system of the human eye basically comprises a cornea, a lens, and a retina. If the lens becomes opaque because of a cataract, light that enters the eye is blocked by the lens, resulting in reduced, or possibly lost, vision. The treatment for lost vision is to perform an operation to remove the affected lens and implant an artificial intraocular lens (IOL) into the eye. Since the intraocular lens cannot adjust the focal length on its own, the implantation is preceded by the selection of an intraocular lens whose focal length is in a far range, an intermediate range, or a near range. Vision which is recovered by the implanted intraocular lens may be evaluated by estimating the size of an image, etc. with calculations based on the Gullstrand's eye model.

However, the patient is unable to directly perceive, and usually highly anxious about, recovered vision achieved by the implanted intraocular lens. The ophthalmologist has no means for gaining exact evaluations of recovered vision. If the implanted intraocular lens is not satisfactory, then an operation has to be performed again to remove the implanted intraocular lens and implant another intraocular lens. To avoid the second operation, both the patent and the ophthalmologist need to know recovered vision more objectively before an intraocular lens is implanted.

Eyeglass and contact lenses that better match eyes with reduced or distorted vision can be selected if images viewed through the lens can be determined by not only subjective evaluations made by the examinee but also objective judgment. If the examinee is an infant, it is difficult to make the correct selection of an eyeglass or contact lens based on only subjective vision measurements.

The refractive index of the optical material of a lens or the like depends on the wavelength of light passing through the lens. The refractive index becomes greater as the wavelength of light passing through the lens is shorter. Because of this phenomenon, the lens suffers an optical defect known as chromatic aberration.

The refractive indexes of different optical materials vary differently depending on the wavelength of light. For all the different optical materials, the refractive index becomes greater as the wavelength of light passing through the lens is shorter. However, the degree to which the refractive index varies differs from optical material to optical material. The degree to which the refractive index varies depending on the wavelength of light is represented by dispersive power. Generally, the characteristics of a lens are indicated by the Abbe number which is the reciprocal of the dispersive power.

The smaller the Abbe number, the greater the degree to which the refractive index varies depending on the wavelength of light. Therefore, eyeglass lenses that are manufactured and sold have a smaller chromatic aberration at their marginal edge, i.e., smaller color fringes, if the Abbe number indicated on them is greater. In general, an optical material is preferable for use as eyeglass lens if its Abbe number is 40 or greater. If the degree of an eyeglass lens is $1/10$ or more of the Abbe number, then the eyeglass lens suffers significant chromatic aberration.

When the user of eyeglasses selects an eyeglass lens, it is difficult for him to gain an intuitive perception of actual effects of chromatic aberration based on only the Abbe number of the eyeglass lens.

When the user wear eyeglasses, an image in the field of view through the eyeglasses is focused in a highly limited central region, and not in other surrounding regions. However, when the user turns his eye, it is possible for an image to be focused in a wider region. Therefore, for accurately recognizing the optical characteristics of an eyeglass lens, it is necessary for the user to confirm a scenery image in a wide range that can be seen in focus through the eyeglass lens by turning the eye.

The chromatic aberration of an eyeglass lens is perceived more clearly when the user turns his eye through a greater angle. Consequently, it is desirable for the user to confirm a scenery image, including color fringes caused by the chromatic aberration, which can be viewed by turning the eye around the marginal edge of the eyeglass lens.

When the user turns the eye while wearing eyeglasses, the ocular optical system varies, and a retinal image also varies depending on the angle through which the eye is turned. Unless the user understands the manner in which the image is seen when he turns the eye, the user is unable to fully understand the characteristics of the eyeglasses.

If the eyeglass lens is a multifocal lens, then when the user turns the eye, the manner in which an image is seen through the eyeglass lens varies greatly, and the distance up to an object seen through the eyeglass lens differs with the angle through which the eye is turned. For example, when the user wears a multifocal eyeglass lens having a central distant-vision portion and a lower near-vision portion, the user sees a distant object through the central distant-vision portion, and sees a near object through the lower near-vision portion after he has turned the eye downwardly.

SUMMARY OF THE INVENTION

It is therefore an object of the present invention to provide an apparatus for simulating an ocular optical system to simulate a retinal image which would be perceived if an intraocular lens were implanted.

Another object of the present invention is to provide an apparatus for simulating an ocular optical system to simulate a retinal image, including color fringes caused by chromatic aberration, which would be perceived if a lens such as an eyeglass lens were worn.

Still another object of the present invention is to provide a method of simulating an ocular optical system to simulate a retinal image, including color fringes caused by chromatic aberration, which would be perceived if a lens such as an eyeglass lens were worn.

Yet still another object of the present invention is to provide an apparatus for and a method of simulating an ocular optical system to simulate an image that would be seen in a wide angular range by turning the eye if an optical lens such as an eyeglass lens were worn.

A still further object of the present invention is to provide an apparatus for and a method of simulating an ocular optical system to simulate a retinal image which would be perceived depending on the angle through which the eye would be turned.

To achieve the above objects, there is provided in accordance with the present invention an apparatus for simulating an ocular optical system to simulate a retinal image produced by a human eye through an optical lens, comprising point-spread-function calculating means for calculating a point spread function based on optical system data including data of a light source display screen disposed in a given position, data of the optical lens, and data of the human eye which includes a cornea, a pupil, and a retina, and retinal image calculating means for calculating a retinal image based on image data disposed in a given position and the point spread function.

According to the present invention, there is also provided an apparatus for simulating an ocular optical system to simulate a retinal image produced by a human eye through an optical lens, comprising point-spread-function calculating means for calculating point spread functions with respect to a plurality of wavelengths based on optical system data including data of a light source display screen disposed in a given position, and optical system data of the optical lens and the human eye with respect to the wavelengths, and retinal image calculating means for calculating monochromatic retinal images with respect to the wavelengths based on original image data and the point spread functions with respect to the wavelengths.

According to the present invention, there is also provided a method of simulating an ocular optical system to simulate a retinal image produced by a human eye through an optical lens, comprising the steps of dividing original image data disposed in a given position into monochromatic image data with respect to a plurality of wavelengths, calculating point spread functions with respect to the wavelengths based on optical system data including data of a light source display screen disposed in a given position, and optical system data of the optical lens and the human eye with respect to the wavelengths, calculating monochromatic retinal images with respect to the wavelengths based on the monochromatic image data and the point spread functions with respect to the wavelengths, and combining the monochromatic retinal images with respect to the wavelengths into a retinal image.

According to the present invention, there is further provided an apparatus for simulating an ocular optical system to simulate a retinal image produced by a human eye through an optical lens, comprising point-spread-function calculating means for calculating point spread functions with respect to a plurality of view dots on a light source display screen disposed in a given position, based on optical system data of the optical lens and the human eye when the human eye is turned to focus an image of the view dots on a retina of the human eye, and scenery image calculating means for calculating a scenery image in a range which can be seen when the human eye is turned, based on image data and the point spread functions with respect to the view dots.

According to the present invention, there is also provided an apparatus for simulating an ocular optical system to simulate a retinal image produced by a human eye through an optical lens, comprising point-spread-function calculating means for calculating point spread functions based on turned-state optical system data including data of a light source display screen positioned to focus light entered through the optical lens on a retina of the human eye, data of the optical lens disposed in a path of travel of light from the light source display screen, and data of the human eye, when the human eye is turned through an optional angle, and retinal image calculating means for calculating a retinal image generated by image data displayed by the light source display screen and the point spread functions.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Embodiments according to the present invention will be hereinafter described with reference to the drawings.

Figure 1:
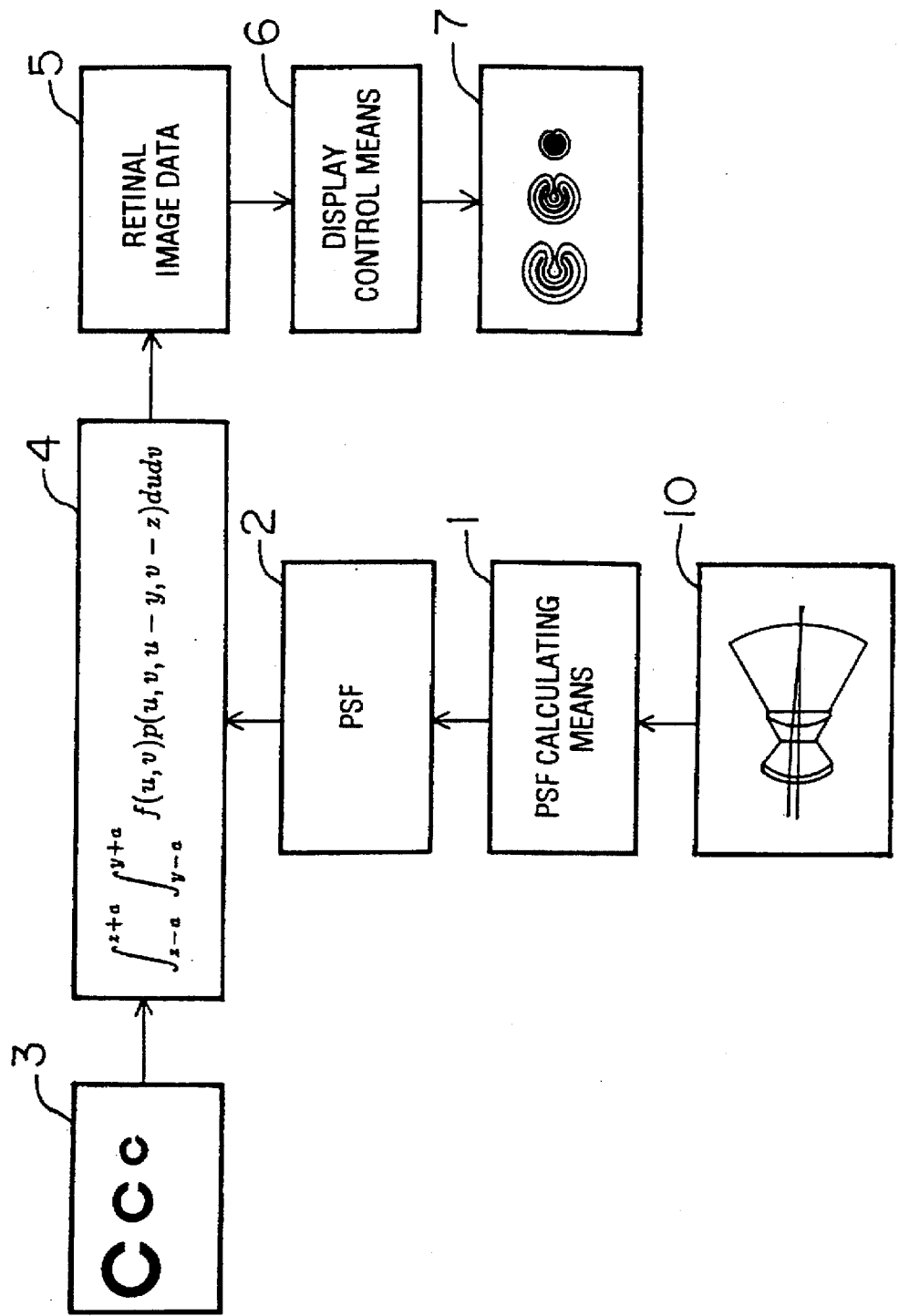
FIG. 1 is a block diagram showing the principles of an apparatus for simulating an ocular optical system according to the present invention.

FIG. 1 shows the principles of an apparatus for simulating an ocular optical system according to the present invention.

According to the present invention, as shown in FIG. 1, optical system data 10 of an ocular optical system including a cornea, a pupil, an intraocular lens, a retina, etc. are determined. The optical system data of the intraocular lens are determined depending on the intraocular lens used. The optical system data of a cornea, a pupil, a retina, etc. are determined using the Gullstrand's eye model. Furthermore, measurable data can be measured directly from the user for whom the apparatus for simulating an ocular optical system is used.

Based on the optical system data 10, PSF (Point Spread Function) calculating means 1 determines a PSF 2. A PSF is a function representing a distribution on an image plane of light emitted from a certain point. The PSF will be described in detail later on.

Retinal image calculating means 4 effects convolutional integration on image data 3 with the PSF 2, determining retinal image data 5. The image data 3 comprise digital image data of a visual mark such as Randolt rings or the like. The retinal image data 5 are converted into display data by display control means 6, which displays a retinal image on a display unit 7 based on the display data. The retinal image displayed on the display unit 7 comprises an image that would be actually formed on the retina of a human eye, and hence provides an accurate objective indication of how the image is seen. The displayed retinal image is blurred as compared with the visual mark represented by the image data 3.

Figure 2:
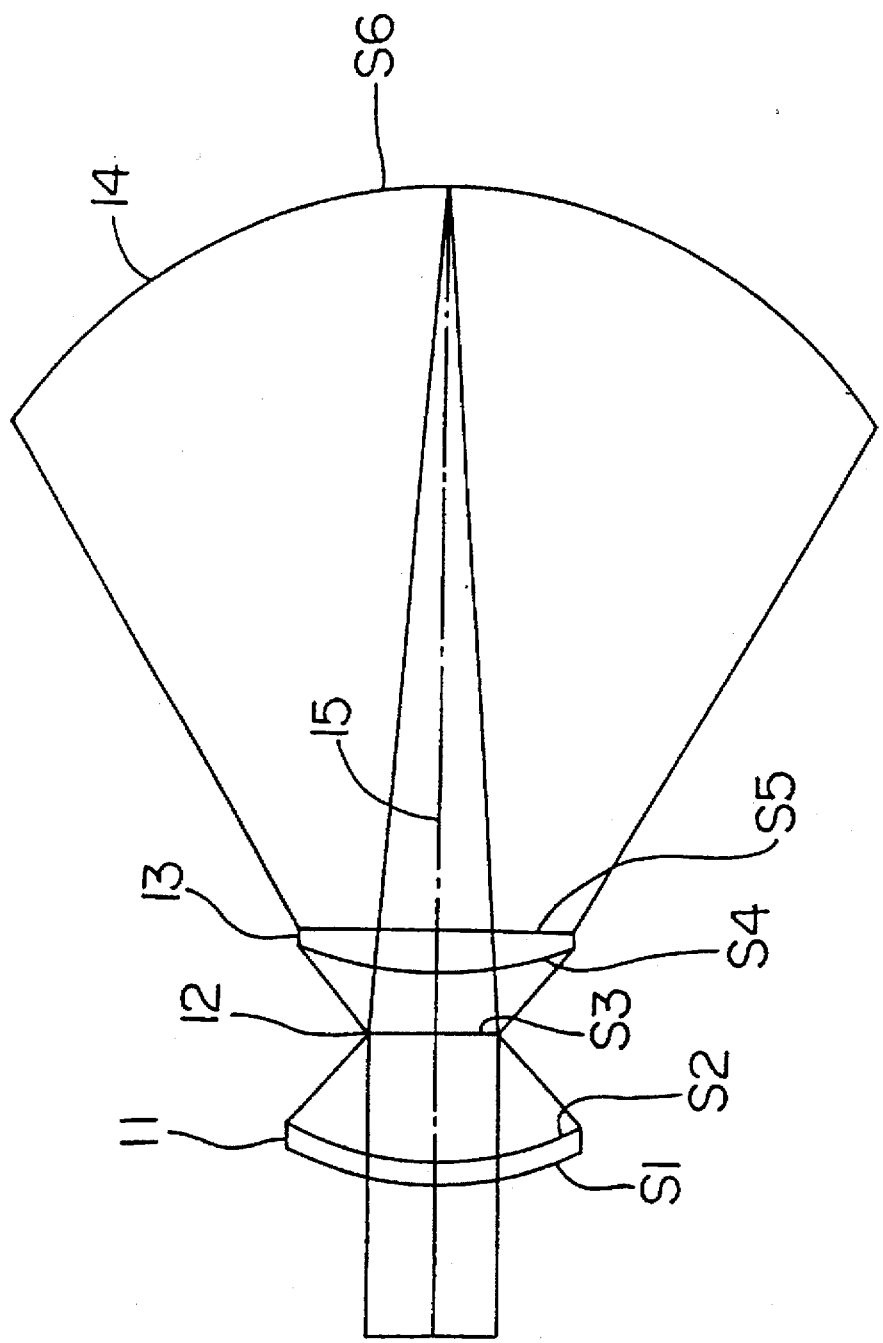
FIG. 2 is a schematic diagram of an ocular optical system including an intraocular lens.

FIG. 2 shows an ocular optical system including an intraocular lens. As shown in FIG. 2, the ocular optical system comprises a cornea 11, a pupil 12, an intraocular lens 13, and a retina 14. The cornea 11 has an outer surface S1 and an inner surface S2. The pupil 12 has a pupil surface S3. The intraocular lens 13 has a convex surface S4 and a flat surface S5. The retina 14 has a retinal surface S6. Optical system data of the ocular optical system shown in FIG. 2 include radii of curvature of the surfaces S1 through S6, surface-to-surface distances from one surface to another, effective radii, and refractive indexes.

A PSF is determined from the optical system data of the ocular optical system shown in FIG. 2. A PSF is a function representing a distribution on an image plane of light emitted from a point on a certain object, and can be determined by tracking n rays of light extending from the point toward the image plane in respective directions and spaced at equal intervals, and determining the density of the rays of light that cross the image plane. Generally, the PSF is determined from the focusing theory of geometrical optics. However, the focusing theory of wave optics must be applied to optical systems with small aberrations and optical systems including a diffraction element, and the PSF is determined by Fresnel integral in such optical systems.

The principles of light ray tracking will be described below. If direction cosines of incident rays of light applied to a certain refractive surface (e.g., one of the surface S1, S2, ... in FIG. 2) and points of intersection between the incident rays and the refractive surface are given, then vectors of normals are determined, and direction cosines of exit rays of light are determined by the Snell's law, so that the exit rays of light are determined. The exit rays of light are incident rays of light applied to a next refractive surface. This process is repeated until points of intersection between the rays of light and a final surface (image plane, e.g., the retinal surface S6 of the retina 14 in FIG. 2) are determined, whereupon the light ray tracking is completed.

Figure 3:
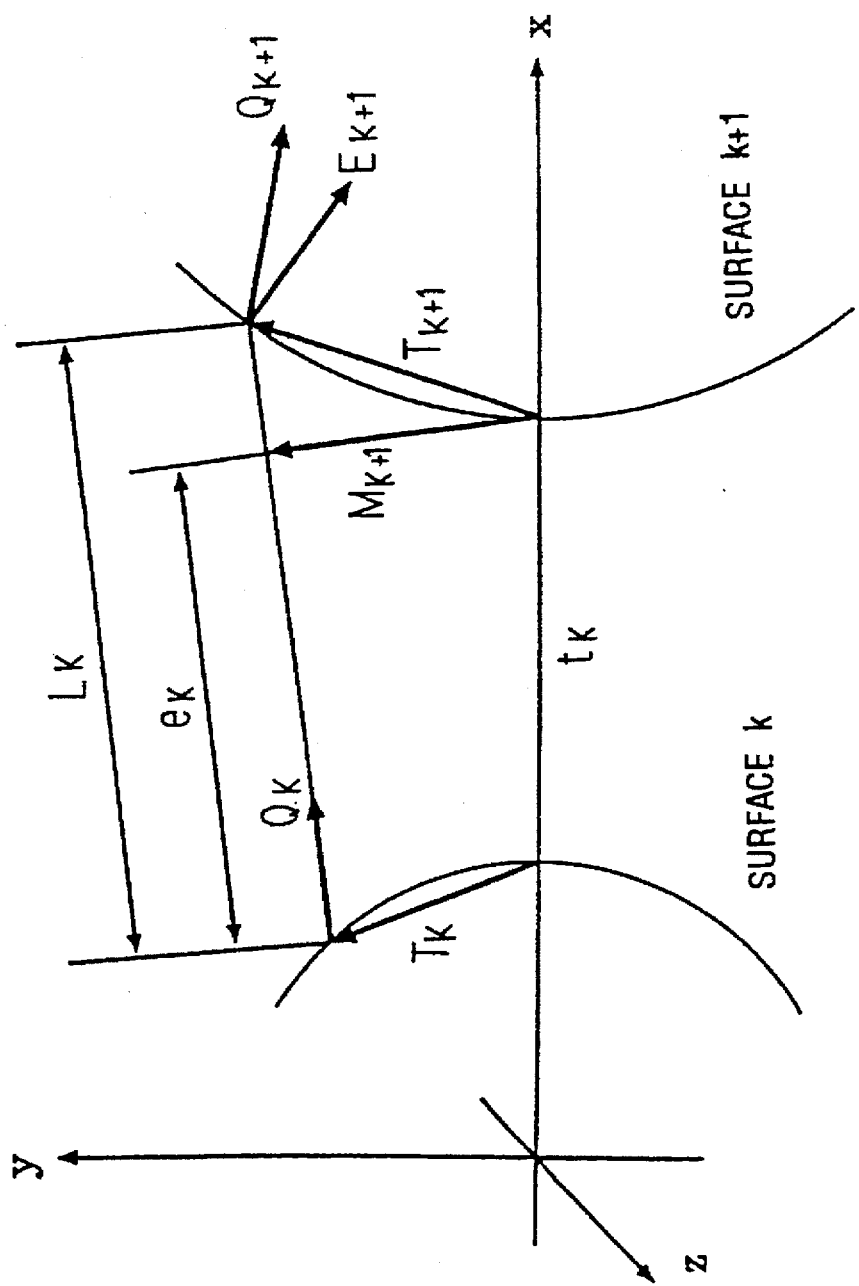
FIG. 3 is a schematic diagram showing the principles of light ray tracking.

A specific process of determining an exit ray of light with respect to an incident ray of light will be described below. FIG. 3 shows the principles of light ray tracking. A ray $Q_k$ of light is directed rightward from a surface k to a surface (k+1), and diffracted by the surface (k+1) into a ray $Q_{k+1}$ of light. Vector relationships according to the following equations (1) are satisfied from the geometrical configuration shown in FIG. 3 and the law of refraction, i.e., the Snell's law:

$$T_k + e_k Q_k = it_k + M_{k+1}$$

$$M_{k+1} + (L_x - e_k) Q_k = T_{k+1}$$

$$T_{k+1} + r_{k+1} E_{k+1} = ir_{k+1}$$

$$(E_{k+1} \times Q_{k+1}) = v_{k+1}(E_{k+1} \times Q_{k+1}) \tag{1}$$

where $r_k$: the radius of curvature of the surface k, which is positive when the curvature is on the right-hand side of the surface;

$c_k = 1/r_k$: the curvature of the surface k;

$t_k$: the distance between the vertexes of the surface k and the surface k+1;

$v_k$: the ratio of the refractive index of a medium on the left-hand side of the surface k to the refractive index of a medium on the right-hand side of the surface k ($v_k = N_k / N_{k+1}$);

$Q_k$: the unit vector ($X_K$, $Y_K$, $Z_K$) (direction cosine) indicative of the direction of the ray of light in the medium on the right-hand side of the surface k;

$T_k$: the vector ($X_K, Y_K, Z_K$) directed from the vertex of the surface k to a point thereon where the incident ray of light is applied;

$E_K$: the unit vector directed toward the center of curvature at the point thereon where the incident ray of light is applied;

$M_{k+1}$: the vector ($M_{k+1,x}, M_{k+1,y}, M_{k+1,z}$) extending from the vertex of the surface k+1 perpendicularly to the unit vector $Q_k$;

$\xi_{k+1}$: the cosine of the angle of incidence at the surface k+1; and $\xi'_{k+1}$: the cosine of the angle of refraction at the surface k+1.

From the equations (1), there are determined equations of transfer from the medium on the left-hand side to the right-hand side of the surface k+1 and refraction at the surface k+1. Specifically, when $Q_k$ ($X_k$, $Y_k$, $Z_k$) and $E_k$ ($x_k$, $y_k$, $z_k$) are given, $E_{k+1}$ ($x_{k+1}$, $y_{k+1}$, $z_{k+1}$) of the surface k+1 is determined according to the following equations (2):

$$e_k = (t_k - x_k)X_k - y_k Y_k - z_k Z_k$$

$$M_{k+1,x} = e_x X_k - (t_k - x_k)$$

$$M^2_{k+1} = (t_k - x_k)^2 + y_k^2 + z_k^2 - e_k^2$$

$$\xi_{k+1} = \sqrt{X_k^2 - c_{k+1}(c_{k+1}M^2_{k+1} - 2M_{k+1,x})}$$

$$L_k = e_k + (c_{k+1}M_{k+1}^2 - 2M_{k+1,x})/(X_k + \xi_{k+1})$$

$$x_{k+1} = x_k + L_k X_k - t_k$$

$$y_{k+1} = y_k + L_k Y_k$$

$$z_{k+1} = z_k + L_k Z_k \qquad (2)$$

Once $E_{k+1}$ ($x_{k+1}$, $y_{k+1}$, $z_{k+1}$) is determined, the direction $Q_{k+1}$ ($x_{k+1}$, $y_{k+1}$, $z_{k+1}$) of a refracted ray of light, i.e., an exit ray of light leaving the surface k+1, is determined according to the following equations (3):

$$\xi'_{k+1} = \sqrt{1 - v_{k+1}^2(1 - \xi_{k+1}^2)}$$

$$g_{k+1} = \xi_{k+1} - v_{k+1}\xi'_{k+1}$$

$$X_{k+1} = v_{k+1}X_k - g_{k+1}c_{k+1}x_{k+1} + g_{k+1}$$

$$Y_{k+1} = v_{k+1}Y_k - g_{k+1}c_{k+1}y_{k+1}$$

$$Z_{k+1} = v_{k+1}Z_k - g_{k+1}c_{k+1}z_{k+1} \qquad (3)$$

In this manner, the ray of light is transferred through and refracted by successive surfaces of the ocular optical system, determining coordinates where the ray of light crosses the final image plane.

According to the present invention, as described above, a retinal image is simulated from the data of an ocular optical system including an optical lens such as an intraocular lens or the like. Therefore, recovered vision of the patient which would be achieved by an implanted intraocular lens can easily be estimated without actually implanting the intraocular lens in the patient.

Since a retinal image can be determined, vision can objectively be determined, allowing the selection of a more appropriate intraocular lens.

Figure 4:
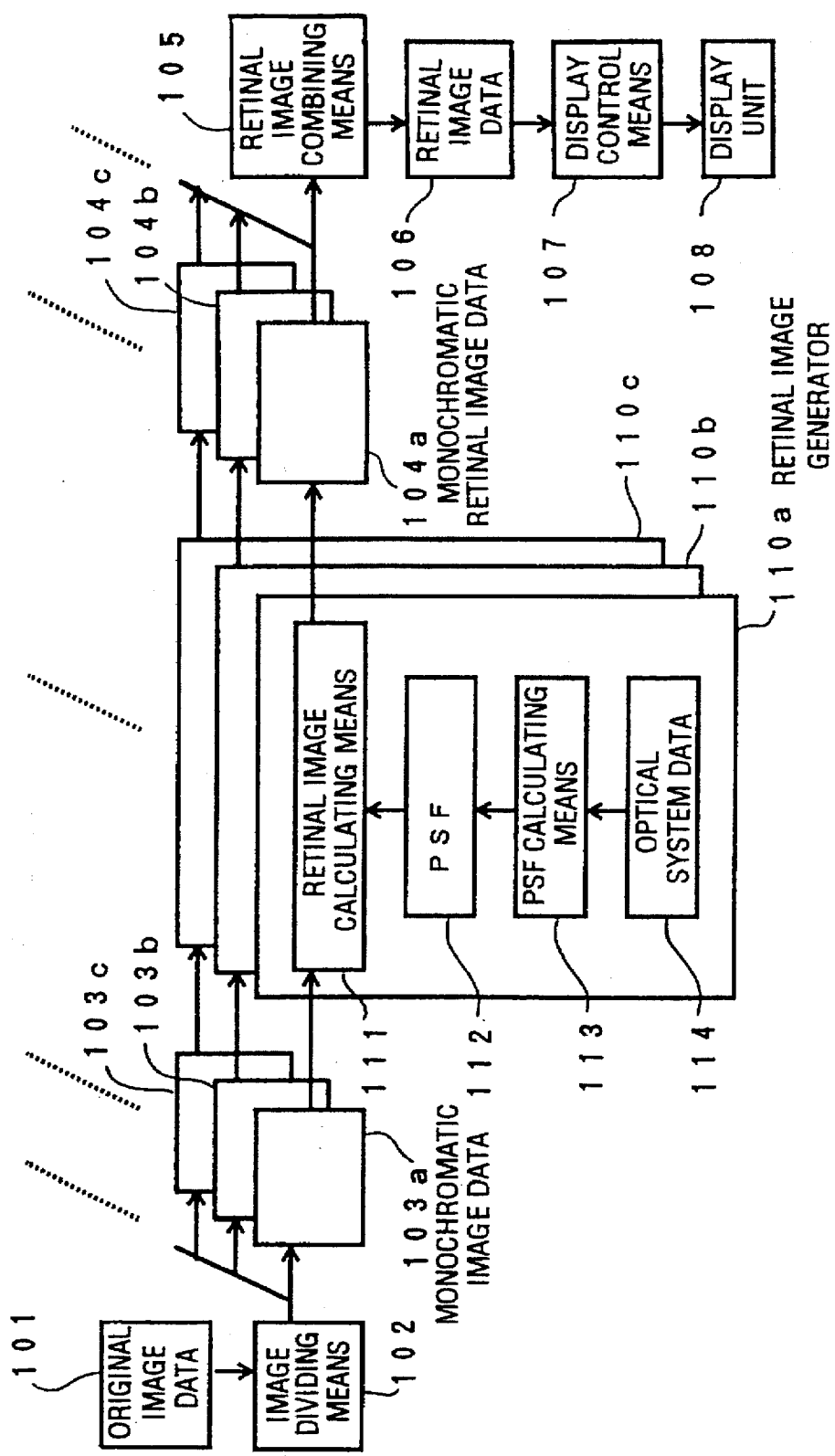
FIG. 4 is a block diagram showing the principles of an apparatus for simulating an ocular optical system, including means for processing data depending on chromatic aberration.

FIG. 4 shows in block form the principles of an apparatus for simulating an ocular optical system, including means for processing data depending on chromatic aberration.

As shown in FIG. 4, original image data 101 to be simulated, which represent a visual mark, are supplied to image dividing means 102. The image dividing means 102 spectrally divides the supplied original image data 101 to be simulated into a plurality of monochromatic image data 103a~103c of respective wavelengths. Each of the monochromatic image data 103a~103c is image data produced when only the spectrum of a certain wavelength is extracted from the original image data 101. Specifically, the original image data 101 are divided into plural image data as respective spectral components at all predetermined wavelengths, and those image data are produced as the monochromatic image data 103a~103c of the predetermined wavelengths. The predetermined wavelengths may be established as desired, and may, for example, be wavelengths spaced at several nm in the wavelength range of visible light.

If the original image data 101 are of single-color data such as black-and-white image data, then the images obtained from the respective spectral components of the original image data 101 are identical in shape to each other. In this case, the original image data 101 may not be spectrally divided, but may be regarded directly as the monochromatic image data 103a~103c of the predetermined wavelengths. Therefore, the image dividing means 102 may be dispensed with. According to this embodiment, however, it is assumed that the original image data 101 are spectrally divided for simulation.

The simulating apparatus has a plurality of retinal image generators 110a~110c for processing the monochromatic image data 103a~103c, respectively. The retinal image generator 110a for processing the monochromatic image data 103a has optical system data 114 which include data of a light source display screen for displaying an image to be simulated, data of an optical lens, and data of a human eye including a cornea, a pupil, a lens, and a retina. The optical data of human eye are basically determined using the Gullstrand's eye model, with the ocular axis length being determined depending on the visual power of the user of the optical lens. The refractive index of the ocular optical system is a refractive index with respect to the wavelength of the monochromatic image data 103a. In this manner, the optical system data 114 are generated with respect to light having a wavelength which enters a human eye having a certain visual power. Measurable data can be measured directly from the user for whom the apparatus for simulating an ocular optical system is used.

The retinal image generator 110a also has PSF calculating means 113 for determining a PSF 112 based on the optical system data 114. The PSF 112 is a function representing a distribution on an image plane of light emitted from a certain point. The retinal image generator 110a further includes retinal image calculating means 111 for effecting convolutional integration on the monochromatic image data 103a with the PSF 112, determining monochromatic retinal image data 104a. A retinal image represented by the monochromatic retinal image data 104a is blurred as compared with the visual mark.

Similarly, the retinal image generators 110b, 110c process the monochromatic image data 103b, 103c, respectively, to produce monochromatic retinal image data 104b, 104c, respectively.

The simulating apparatus further includes retinal image combining means 105 for combining the generated monochromatic retinal image data 104a~104c into retinal image data 106. Since the monochromatic retinal image data 104a~104c have different wavelengths, respectively, the retinal image data 106 represent a retinal image that contains image components which will be displayed at different positions because of chromatic aberration. The retinal image data 106 are supplied to display control means 107, which then displays a retinal image based on the supplied retinal image data 106 on the display screen of a display unit 108. The retinal image displayed on the display unit 108 contains image components produced due to chromatic aberration, and hence provides an accurate objective indication of how the visual mark is seen.

A simulating process carried out by the simulating apparatus shown in FIG. 4 will be described in greater detail below.

Original color image data of a visual mark, which are to be displayed for simulation, are generated, and optical system data are established for simulation. In the example given below, the original color image data are divided into monochromatic image data of three spectral lines, i.e., F-line, d-line, and C-line, for simulation.

The Abbe number $v_d$ with respect to the d-line is defined according to the following equation (4):

$$v_d = (n_d - 1)/(n_F - n_c) \quad (4)$$

where $n_d$ is the refractive index of a medium with respect to the d-line (589 nm), $n_F$ the refractive index of a medium with respect to the F-line (486 nm), and $n_c$ the refractive index of a medium with respect to the C-line (656 nm).

Figure 5:
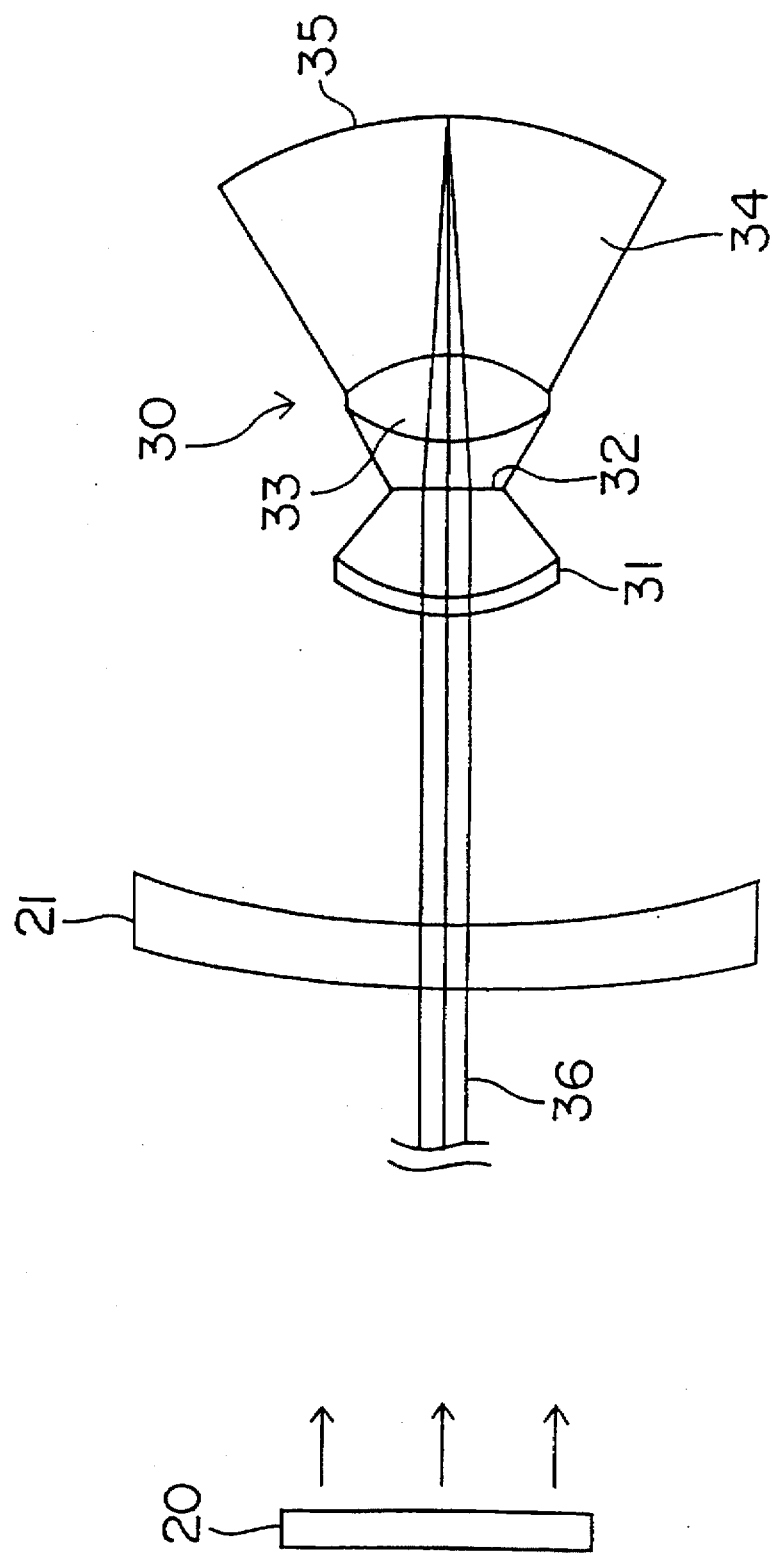
FIG. 5 is a schematic diagram of an ocular optical system according to a first embodiment of the present invention.

FIG. 5 shows an ocular optical system according to a first embodiment of the present invention. The ocular optical system shown in FIG. 5 includes eyeglasses for correcting the vision of the user. A ray 36 of light emitted from a light source display screen 20 which displays original image data passes through an eyeglass lens 21 and enters a human eye 30. The human eye 30 directly faces the light source display screen 20, and has a cornea 31 on its front. The human eye 30 also has a pupil 32 positioned behind the cornea 31 for restricting the amount of light entering the human eye 30, a lens 33 positioned behind the pupil 32, a vitreous humor 34 positioned behind the lens 33, and a retina 35 positioned behind the vitreous humor 34. The human being detects light that has entered the human eye 30 and recognizes an image produced by the light through the retina 35.

Based on the ocular optical system shown in FIG. 5, optical system data are generated with respect to predetermined wavelengths of light that enters the human eye 30. First, the distance up to the light source display screen 20 is determined. This distance is assumed to be infinitely far, and hence parallel rays of light from the light source display screen 20 enter the eyeglass lens 21.

The eyeglass lens 21 comprises a lens having a degree depending on the visual power of the user of the eyeglass lens 21. The Abbe number of the eyeglass lens 21 is determined when the material of the eyeglass lens 21 is specified. The eyeglass lens 21 has a front convex surface and a rear concave surface. The radii of curvature of these front convex and rear concave surfaces of the eyeglass lens 21, and the thickness of the eyeglass lens 21 are equal to corresponding design values of a lens to be simulated. A distance from the eyeglass lens 21 up to the cornea 31 is established.

Optical data relative to the human eye 30 are generated using the Gullstrand's eye model. However, since the ocular optical system is simulated for vision corrected by eyeglasses, the human eye 30 needs to be far-sighted or near-sighted. Therefore, only the ocular axis length of the human eye 30 or the curvature of the convex surface of the cornea 31 is set to a value depending on the visual power of the user. The Abbe number of the optical system of the human eye 30 is infinite. In this manner, the optical system data relative to the human eye 30 having any optional visual power are generated with respect to predetermined wavelengths of light.

After the original image data and the optical system data are generated as described above, the ocular optical system is simulated on the basis of the generated data.

Figure 6:
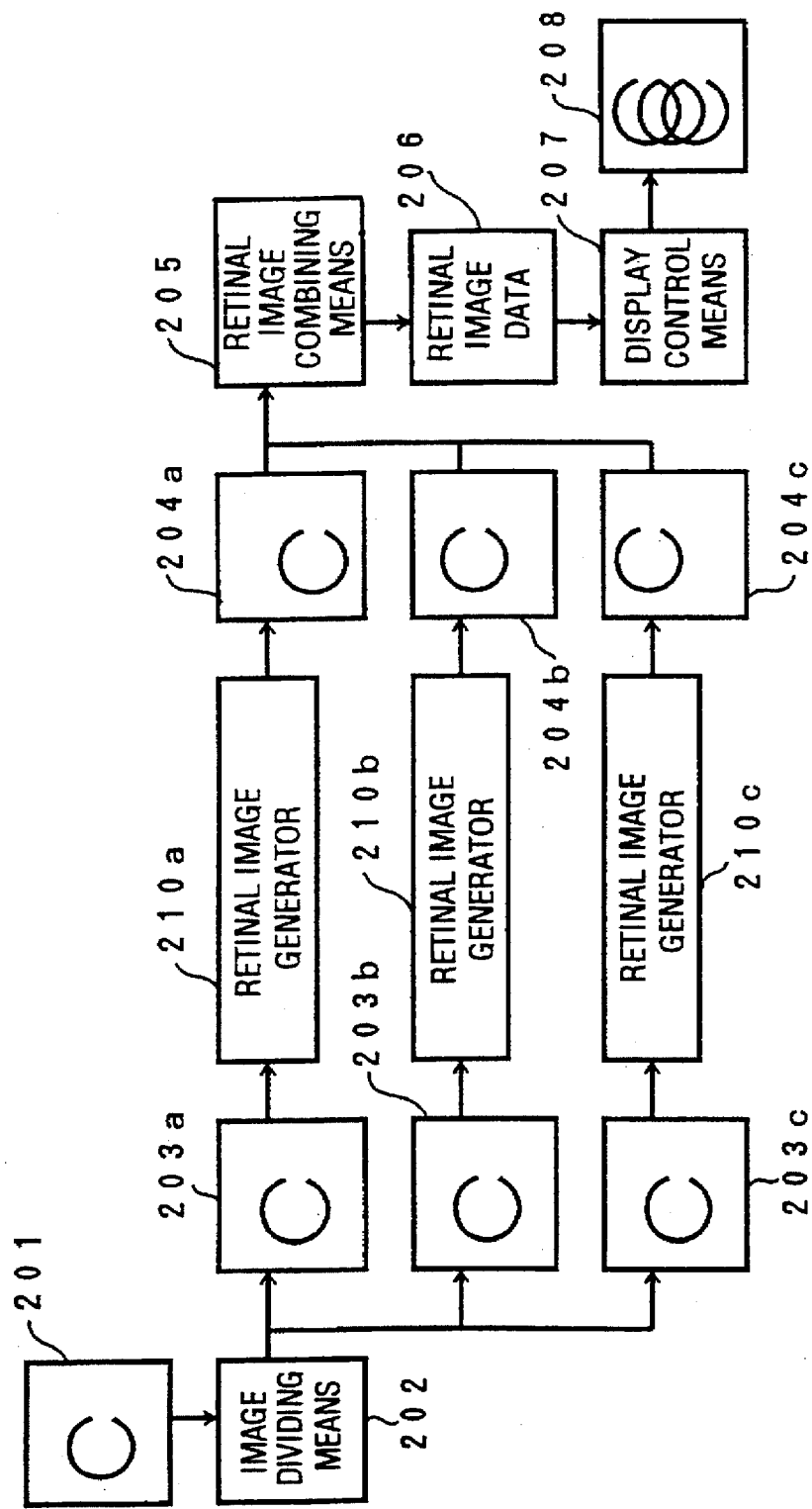
FIG. 6 is a block diagram of an apparatus for simulating an ocular optical system according to the first embodiment.

FIG. 6 shows in block form an apparatus for simulating an ocular optical system according to the first embodiment. As shown in FIG. 6, the simulating apparatus has image dividing means 202 for dividing original image data 201 into monochromatic image data 203a~203c of three colors, i.e., C-line (red), d-line (yellow), and F-line (blue). The d-line monochromatic image data are actually yellow image data, but will be handled as green image data.

The simulating apparatus also has retinal image generators 210a~210c in which respective PSF calculating means calculate PSFs for the respective wavelengths based on the optical system data that have been generated with respect to the C-line, the d-line, and the F-line, respectively. The retinal image generators 210a~210c have respective retinal image calculating means for effecting convolutional integration on the monochromatic image data 203a~203c with the corresponding PSFs to generate monochromatic retinal image data 204a~204c with respect to the respective wavelengths. If it is assumed that a light intensity distribution of an ideal image on the image plane is represented by f(y, z) and a PSF at a point (y, z) by p (x, y, u, v), then the light intensity at the point (y, z) on the retina 35 is expressed by the following equation (5):

$$g(y,z) = \int_{x-a}^{x+a} \int_{y-a}^{y+a} f(u,v)p(u,v,u-y,v-z)dudv \quad (5)$$

where p(u, v, u−y, v−z) is a value of PSF at a point that is spaced from a point (u, v) by (u−y, v−z), and a is a radius of spread of the PSF. When the light intensities at all points on the retina 35 are determined according to the equation (5), the monochromatic retinal image data 204a~204c are generated with respect to the respective wavelengths. Retinal images displayed based on the monochromatic retinal image data 204a~204c have their coordinate positions shifted from each other because of chromatic aberration.

The monochromatic retinal image data 204a~204c thus generated are combined into retinal image data 206 by retinal image combining means 205. The retinal image data 206 are supplied to display control means 207, which then displays a retinal image based on the supplied retinal image data 206 on the display screen of a display unit 208. Since the retinal image displayed on the display unit 208 contains image components produced due to chromatic aberration, effects of chromatic aberration on the image formed on the retina by the rays of light that have passed through the ocular optical system can be simulated on the display screen of the display unit 208.

In the above first embodiment, the human eye faces directly toward the light source display screen, i.e., the light from the light source display screen passes through the central region of the eyeglass lens into the human eye. However, it is possible to simulate an ocular optical system when the human eye is turned. When the human eye is turned, the light emitted from the light source display screen is applied to the marginal edge of the eyeglass lens at a certain angle, causing the chromatic aberration of the eyeglass lens to have a large effect on the light passing therethrough. A specific simulation of an ocular optical system with the human eye being turned will be described below.

Figure 7:
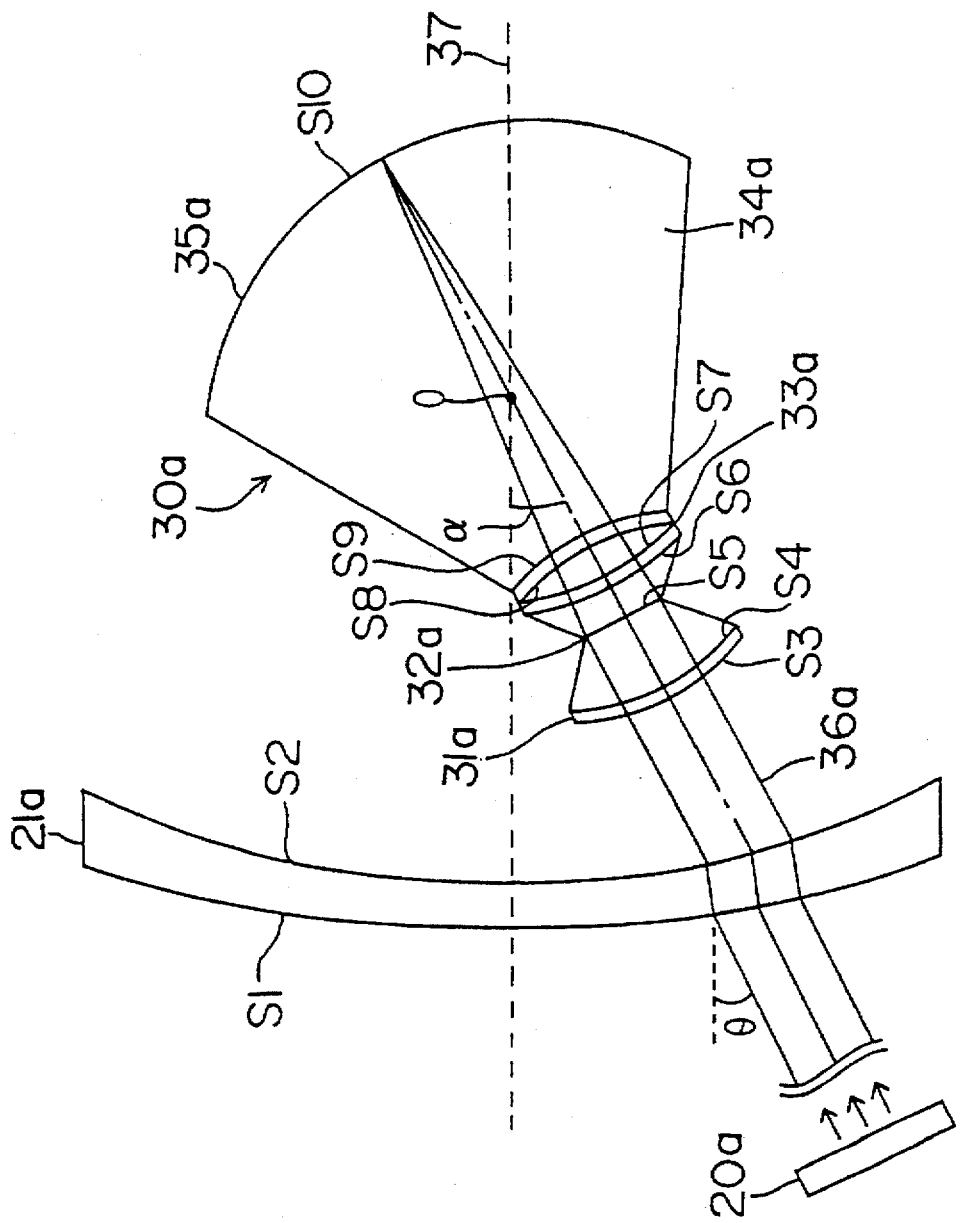
FIG. 7 is a schematic diagram of an ocular optical system according to a second embodiment of the present invention.

FIG. 7 shows an ocular optical system according to a second embodiment of the present invention. In the ocular optical system shown in FIG. 7, the human eye is turned from its forward-facing position.

In FIG. 7, a straight reference axis 37 extends through the center of an eyeglass lens 21a and the center ○ about which a human eye 30a is turned. A light source display screen 20a is positioned below the reference axis 37. A ray 36a of light emitted from the light source display screen 20a passes through the eyeglass lens 21a obliquely and enters the human eye 30a. The human eye 30a directly faces the light source display screen 20a, and has a cornea 31a on its front. The human eye 30a also has a pupil 32a positioned behind the cornea 31a for restricting the amount of light entering the human eye 30a, a lens 33a positioned behind the pupil 32a, a vitreous humor 34a positioned behind the lens 33a, and a retina 35a positioned behind the vitreous humor 34a.

The ocular optical system shown in FIG. 7 has various surfaces associated with its components referred to above.

Specifically, the eyeglass lens 21a has a front surface S1 and a rear surface S2. The cornea 31a has a front surface S3 and a rear surface S4. The pupil 32a has a pupil surface S5. The lens 33a has a first front surface S6, a first rear surface S7, a second front surface S8, and a second rear surface S9. The retina 35a has a retina surface S10. These surfaces S1~S10 have various data described in Table 1 shown below.

TABLE 1

| Medium/ Surface | Radius of Curvature | Effective Radius | Thickness | Refractive index for d-line | Thickness Subtotal |
|---|---|---|---|---|---|
| Air |  |  | 0.00000 | 1.00000 | 0.000 |
| S1 | 148.23116 | 37.500 |  |  |  |
| Eyeglass lens |  |  | 1.30000 | 1.59500 | 1.300 |
| S2 | 84.67343 | 37.500 |  |  |  |
| Air |  |  | 12.00000 | 1.00000 | 13.300 |
| S3 | 7.70000 | 5.000 |  |  |  |
| Cornea |  |  | 0.50000 | 1.37600 | 13.800 |
| S4 | 6.80000 | 5.000 |  |  |  |
| Anterior chamber |  |  | 2.50000 | 1.33600 | 16.300 |
| S5 | (planar) | 2.500 |  |  |  |
| Posterior chamber |  |  | 0.60000 | 1.33600 | 16.900 |
| S6 | 10.00000 | 3.800 |  |  |  |
| Lens |  |  | 0.54600 | 1.38600 | 17.446 |
| S7 | 7.91100 | 3.800 |  |  |  |
| Lens |  |  | 2.41900 | 1.40600 | 19.865 |
| S8 | -5.76000 | 3.800 |  |  |  |
| Lens |  |  | 0.63500 | 1.38600 | 20.500 |
| S9 | -6.00000 | 3.800 |  |  |  |
| Vitreous |  |  | 18.36408 | 1.33600 | 38.864 |
| S10 | -12.56408 | 10.000 |  |  |  |
| Retina |  |  | 0.00000 | 1.33600 | 38.864 |

In Table 1 above, the radii of curvature, the effective radii, the thicknesses, and the thickness subtotals are expressed in [mm]. The Abbe number of the eyeglass lens is $v_d = 32$.

The direction in which the light travels from the light source display screen 20a is angularly spaced from the reference axis 37 by an angle θ of 30°. Since the light from the light source display screen 20a is refracted by the eyeglass lens 21a, the human eye 30a is turned an angle α of 27.7°.

Original image data used to simulate the ocular optical system shown in FIG. 7 are produced from an image of a visual mark which comprises Randolt rings.

Figure 8:
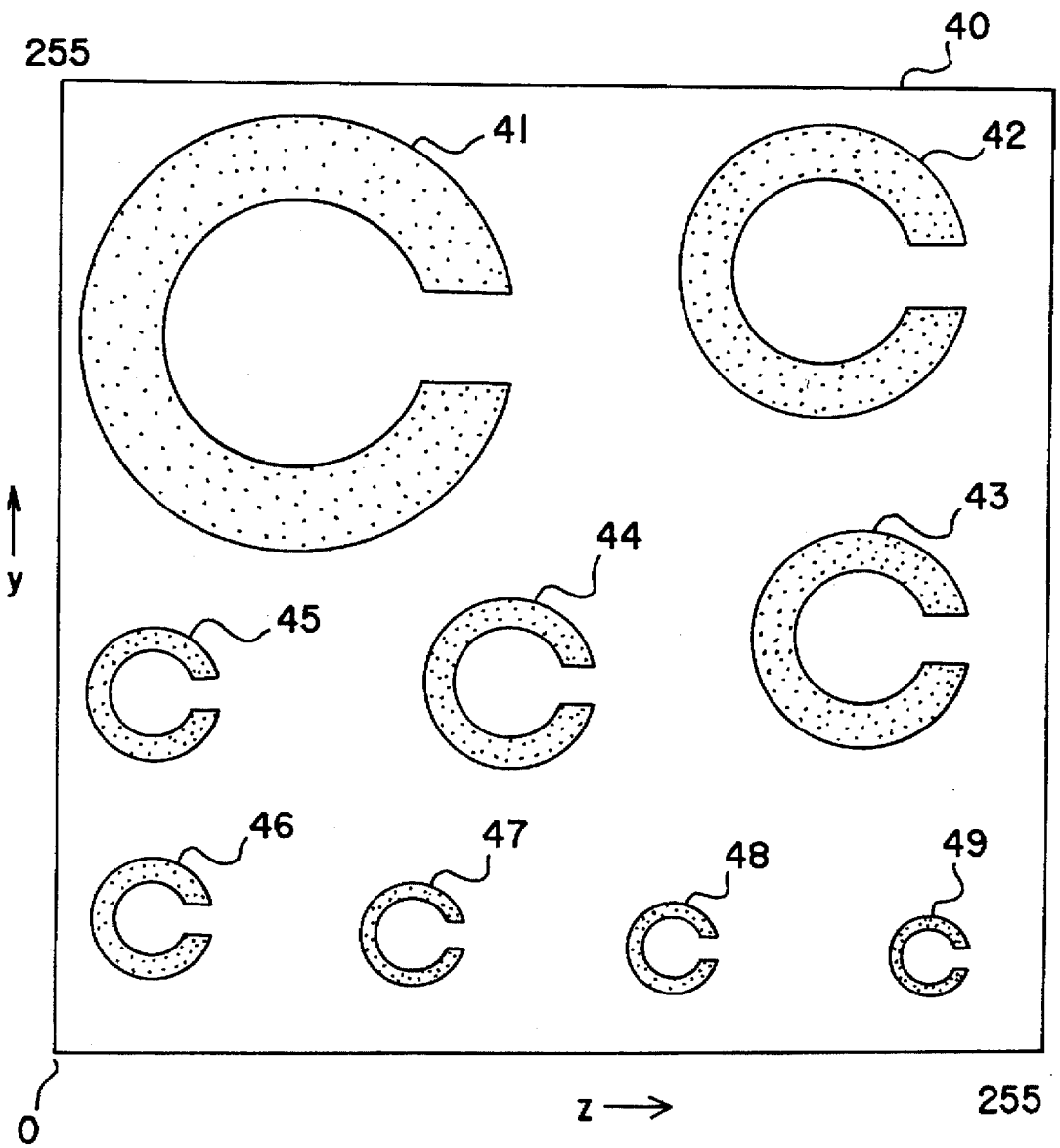
FIG. 8 is a view of Randolt rings used as an image.

FIG. 8 shows an image of Randolt rings 40. The Randolt rings 40 comprise a ring 41 for visual power 0.2, a ring 42 for visual power 0.3, a ring 43 for visual power 0.4, a ring 44 for visual power 0.5, a ring 45 for visual power 0.6, a ring 46 for visual power 0.7, a ring 47 for visual power 0.8, a ring 48 for visual power 0.9, and a ring 49 for visual power 1.0. The Randolt rings 40 have an overall size of 250×250 pixels which are spaced at intervals of 0.001 mm. The Randolt rings 40 are drawn in black against a white background.

The image data of the Randolt rings 40 are divided into monochromatic image data of three spectral lines, i.e., F-line, d-line, and C-line, for simulation.

Figure 9:
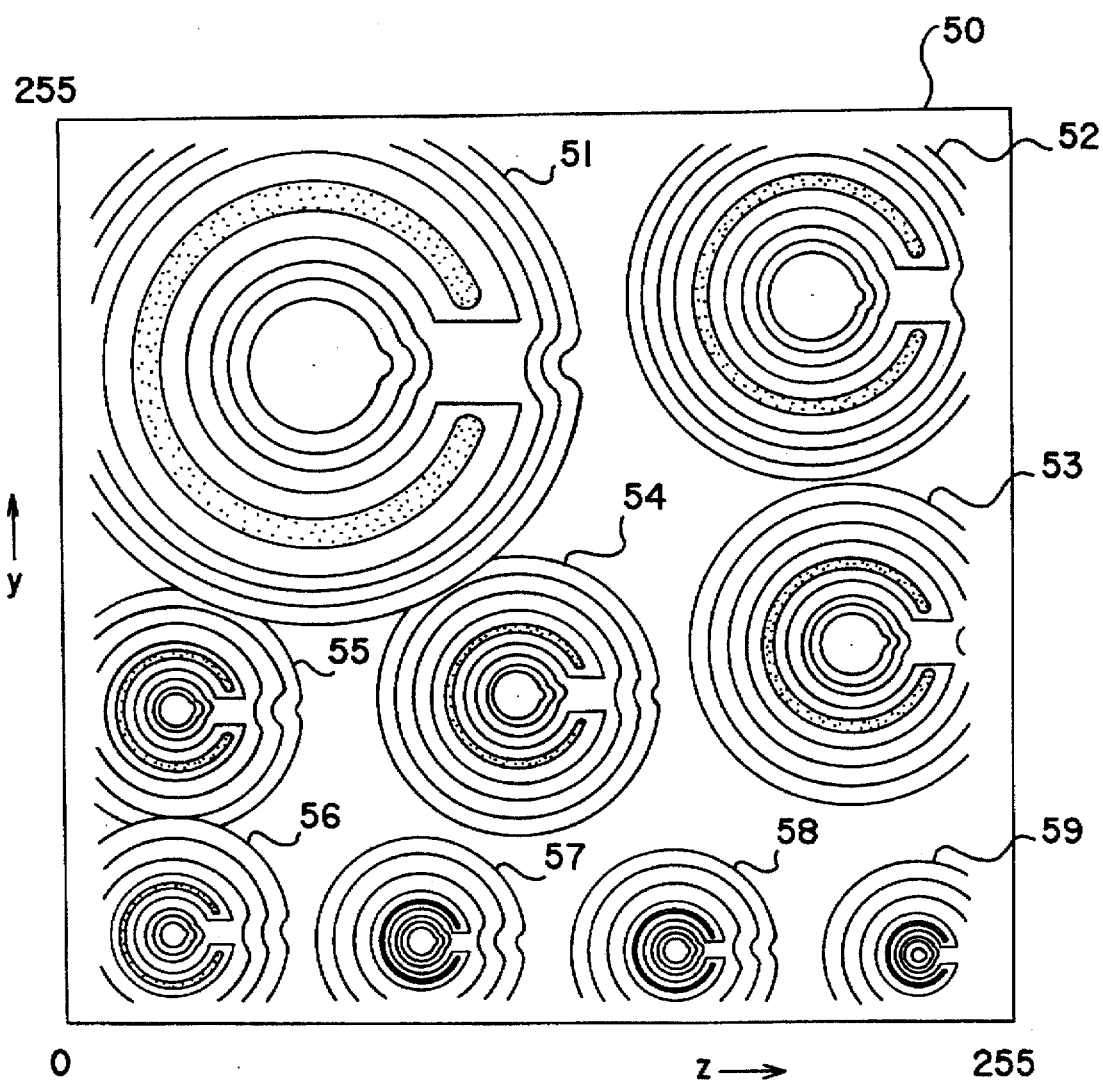
FIG. 9 is a view of a monochromatic retinal image produced from F-line monochromatic image data.

FIG. 9 shows a monochromatic retinal image 50 produced from the monochromatic image data of the F-line. The monochromatic retinal image 50 comprises retinal images 51~59 corresponding respectively to the Randolt rings 41~49 shown in FIG. 8. Actually, the retinal images 51~59 are viewed as blurred images having a continuously varying density. In FIG. 9, such a continuously varying density of each of the retinal images 51~59 is expressed by contour lines such that the density is progressively greater toward the center of the retinal images, or progressively smaller toward the outer edge of the retinal images.

Monochromatic retinal images produced from the monochromatic image data of the d-line and the C-line are essentially the same as the monochromatic retinal image 50 shown in FIG. 9, except that their coordinates along the Y-axis differ slightly from each other.

Figure 10:
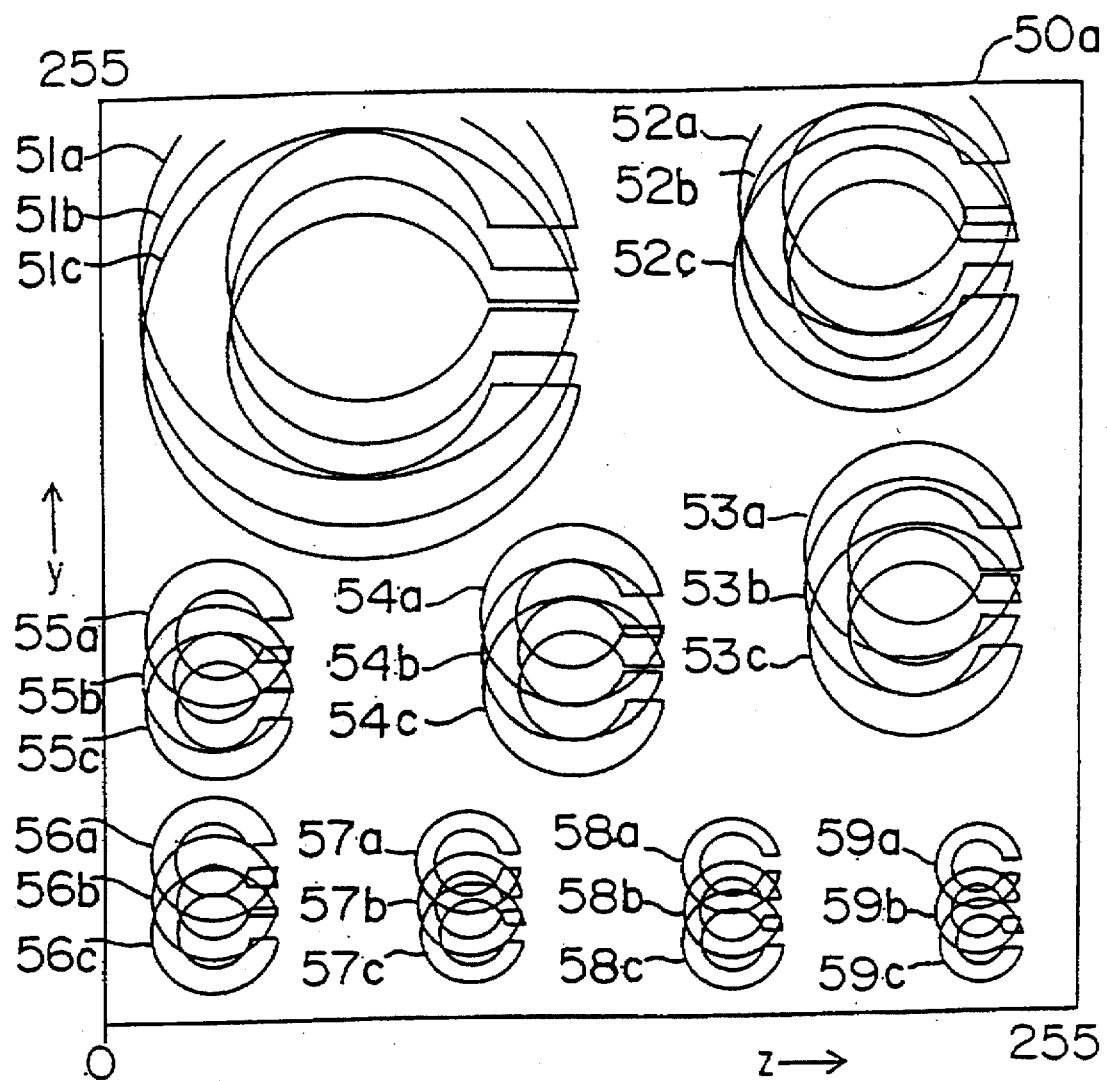
FIG. 10 is a view of a retinal image composed of combined monochromatic retinal images.

FIG. 10 shows a retinal image 50a composed of the monochromatic retinal images which are combined with each other. In FIG. 10, the monochromatic retinal images are indicated by the profiles of ideal retinal images, but actually are blurred images about the contour lines as shown in FIG. 9.

The retinal image 50a is composed of retinal images 51a~59a of the F-line (blue), retinal images 51b~59b of the d-line (green), and retinal images 51c~59c of the C-line (red). As shown in FIG. 10, these retinal images of the F-line, the d-line, and the C-line are shifted from each other. The portions of the retinal images of the F-line (blue) which are shifted out of overlapping relation to the other retinal images are colored in yellow (complementary to blue). The portions of the retinal images of the d-line (green) which are shifted out of overlapping relation to the other retinal images are colored in purple (complementary to green). The portions of the retinal images of the C-line (red) which are shifted out of overlapping relation to the other retinal images are colored in pale aqua (complementary to red). The degree to which the colors of the retinal images are shifted from each other depends on the Abbe number. Therefore, when the user wears an eyeglass lens having a different Abbe number, the degree of a shift in the colors due to chromatic aberration can objectively be recognized.

In this embodiment, the original image data are divided into monochromatic image data of three spectral lines, and the retinal image data are generated from the monochromatic image data. However, the original image data may be divided into monochromatic image data of a greater number of spectral lines, and these monochromatic image data may be combined into retinal image data.

For example, the original image data may be divided into monochromatic image data at spectral intervals of 5 nm in a wavelength range from 380 nm to 780 nm, and monochromatic retinal image data generated from the divided image data may be combined into final retinal image data. The color matching functions are used for combining the monochromatic retinal image data.

In an RGB trichromatic system which employs the color matching functions, the value of a stimulus applied to photoreceptors at the time light at a certain wavelength reaches the retina is indicated by the intensities of three spectral lines, i.e., R (700 nm), G (546.3 nm), and B (435.8 nm). Stated otherwise, the color matching functions make it possible to specify the intensities of lights R, G, B for replacing light in any optional color with three lights R, G, B to enable the human eye to sense the color.

In the RGB trichromatic system, one of the three values may possibly be negative. Therefore, it is the general practice to use an XYZ trichromatic system which employs reference stimuli X, Y, Z capable of color matching by adding positive values of reference stimuli R, G, B. Specifically, stimulus values are determined with respect to the F-line, the d-line, and the C-lines in the XYZ trichromatic system, and thereafter converted into corresponding values in the RGB trichromatic system for determining intensities of the RGB spectral lines. Stated otherwise, the monochromatic retinal image data are converted into data of the RGB spectral lines, and the intensities at the coordinates of the RGB spectral lines are added to produce retinal image data.

Since the original image data are divided into many monochromatic image data, an image that is produced by a simulation is made close to an image which will actually be formed on the retina.

In the above embodiment, the ocular optical system includes an eyeglass lens as an optical lens to be worn by the user. However, the ocular optical system may include a contact lens or an intraocular lens as an optical lens for producing a simulated image. Use of such ocular optical system is effective to select an appropriate contact lens or intraocular lens.

In the above embodiment, the original image data are divided into monochromatic image data of the d-line, the F-line, and the C-line, which are used to define an Abbe number with respect to the d-line, and these monochromatic image data are processed to generate monochromatic retinal image data. However, the original image data may be divided into monochromatic image data of other spectral lines. For example, the original image data may be divided into monochromatic image data of an e-line (540.07 nm), an F'-line (479.99 nm), and a C'-line (643.85 nm), which are used to define an Abbe number with respect to the e-line, and these monochromatic image data are processed to generate monochromatic retinal image data. The Abbe number $v_e$ with respect to the e-line is defined according to the following equation (6):

$$v_e = (n_e - 1)/(n_{F'} - n_{C'}) \qquad (6)$$

In the above embodiment, the light source display screen is positioned at an infinitely far distance. However, the light source display screen may instead be positioned at a close distance.

A plurality of retinal images generated from optical system data representing a plurality of optical lenses having different Abbe numbers may be displayed simultaneously on the display unit. Such a display mode allows the user to compare, with ease, different views which are obtained through the optical lens due to their different Abbe numbers.

In the above embodiment, optical system data established with respect to a plurality of wavelengths are used, monochromatic retinal image data with respect to the respective wavelengths are generated from original image data, and the monochromatic retinal image data are combined into retinal image data. Consequently, a retinal image which reflects chromatic aberration of an optical lens that is to be worn by the user can be simulated. As a result, the user can objectively confirm different views of an image which are caused by different Abbe numbers of optical lenses without actually wearing those optical lenses as eyeglass lenses.

Figure 11:
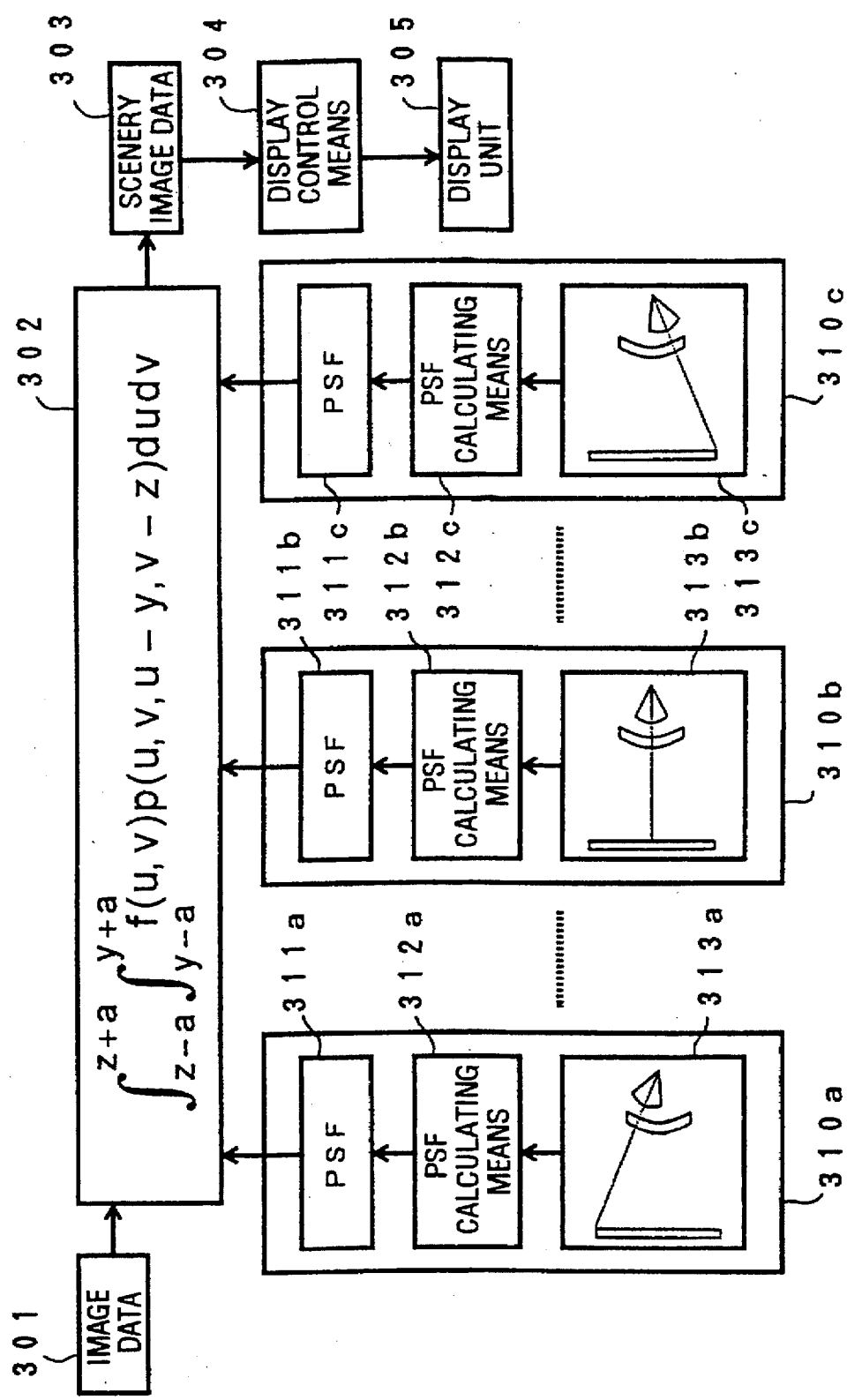
FIG. 11 is a block diagram showing the principles of an apparatus for simulating an ocular optical system, including means for processing data depending on the turning of a human eye.

FIG. 11 shows in block form the principles of an apparatus for simulating an ocular optical system, including means for processing data depending on the turning of a human eye. The simulating apparatus shown in FIG. 11 includes a light source display screen which is so large that the user cannot view the light source display screen in its entirety unless he turns his eye. The light source display screen displays a matrix of view dots. The simulating apparatus also has a plurality of PSF calculating units 310a~310c associated with the respective view dots. For example, if the light source display screen can be divided into a vertical array of m pixels or view dots and a horizontal array of n pixels or view dots, i.e., a matrix of m×n pixels or view dots, then the simulating apparatus has m×n PSF calculating units.

The PSF calculating units 310a~310c contain optical system data 313a~313c, respectively, which are generated when the user has turned his eye in order to focus the images of the corresponding view dots on the retina. The optical system data 313a~313c include positional data of the corresponding view dots, data of an optical lens including curvatures of convex and concave surfaces thereof, a refractive index thereof, and data of a human eye including a cornea, a pupil, a lens, a retina, and the angle through which the human eye is turned. The data of the optical lens can be determined by corresponding design values of the lens. The data of the human eye are basically determined using the Gullstrand's eye model, with the ocular axis length being determined depending on the visual power of the user of the optical lens. Furthermore, measurable data can be measured directly from the user for whom the apparatus for simulating an ocular optical system is used.

Based on the optical system data 313a~313c, PSF calculating means 312a~312c determine PSFs 311a~311c, respectively. Each of the PSFs 311a~311c is a function representing a distribution on an image plane of light emitted from a certain view dot.

The simulating apparatus also includes scenery image calculating means 302 for effecting convolutional integration on image data 301 displayed on the light source display screen with the PSFs 311a~311c, thereby generating scenery image data 303. The simulating apparatus further includes display control means 304 for displaying an image represented by the scenery image data 303 on a display unit 305. The display unit 305 now displays on its display screen an overall image that can be visually recognized by the user when he moves the eye vertically and horizontally.

A simulating process carried out by the simulating apparatus shown in FIG. 11 will be described in greater detail below.

Figure 12:
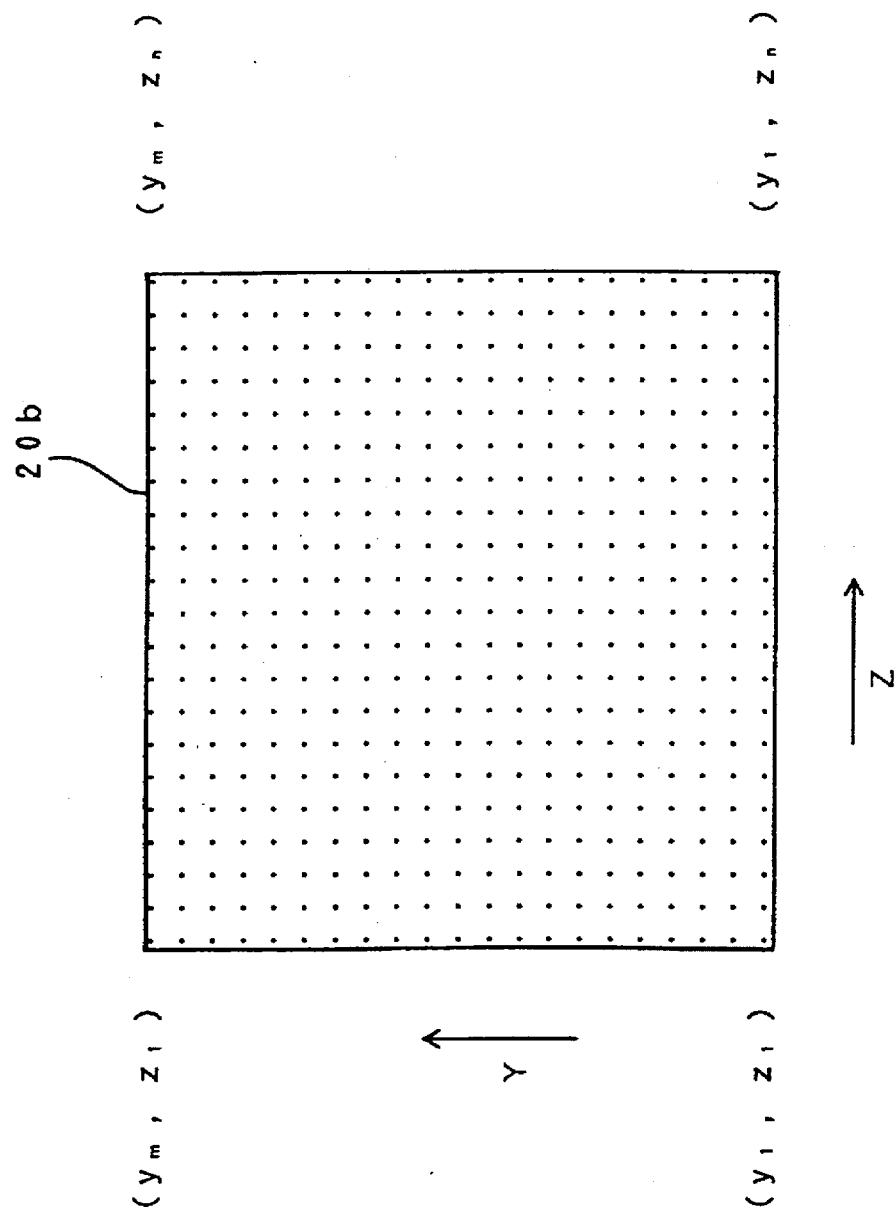
FIG. 12 is a view of a light source display screen.

Image data to be displayed for simulation are generated. The image data are displayed on the light source display screen in a range which can be focused when the user turns his eye. FIG. 12 shows the light source display screen, denoted by 20b. The light source display screen 20b comprises a flat surface extending perpendicularly to the X-axis and has its center positioned on the X-axis. The light source display screen 20b is positioned at an infinitely far distance from the human eye. The light source display screen 20b is composed of a Y-axis array of m pixels ($y_1$~$y_m$) and a Z-axis array of n pixels ($z_1$~$z_n$). Therefore, the light source display screen 20b has a matrix of m×n view dots. Image data of any optional configuration are generated by applying an intensity of light to each of the view dots on the light source display screen 20b. The light applied to each of the view dots may be monochromatic light or lights having respective plural wavelengths.

Figure 13:
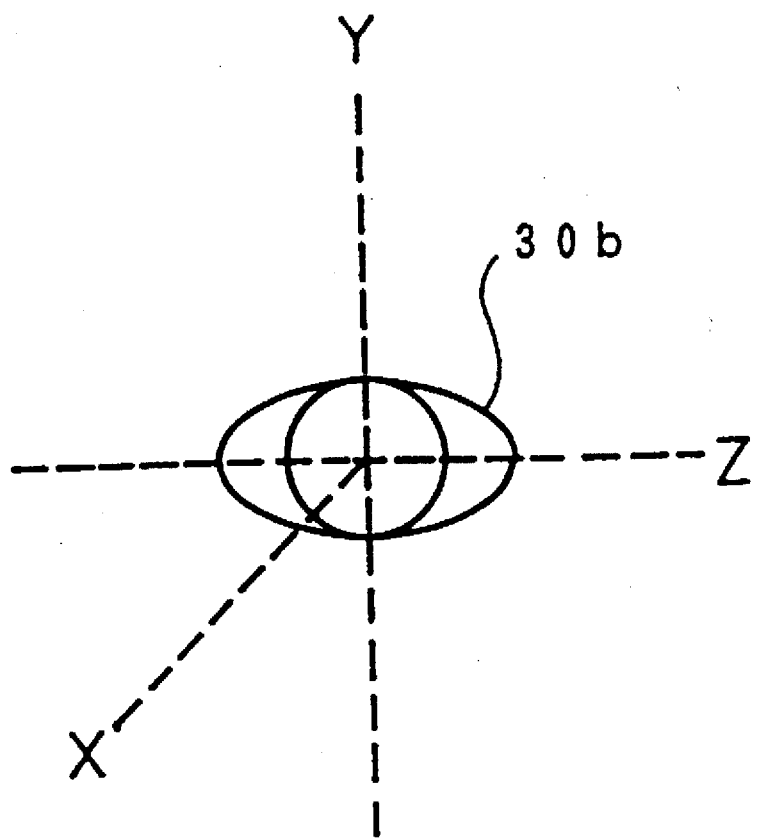
FIG. 13 is a view of a human eye.

FIG. 13 shows a human eye 30b as viewed from the light source display screen 20b in the positive direction of the X-axis. The center around which the human eye 30b is turned is positioned on the X-axis. Therefore, when the human eye 30b is directed parallel to the X-axis, the human eye 30b views the center of the light source display screen 20b. For viewing any optional view dot on the light source display screen 20b, the human eye 30b is turned in the directions of the Y-axis and the Z-axis. If the human eye 30b is turned in the direction of the Y-axis through an angle $\alpha_y$, and in the direction of the Z-axis through an angle $\alpha_z$, then the angles $\alpha_y$, $\alpha_z$ are associated with all the view dots on the light source display screen 20b.

Figure 14:
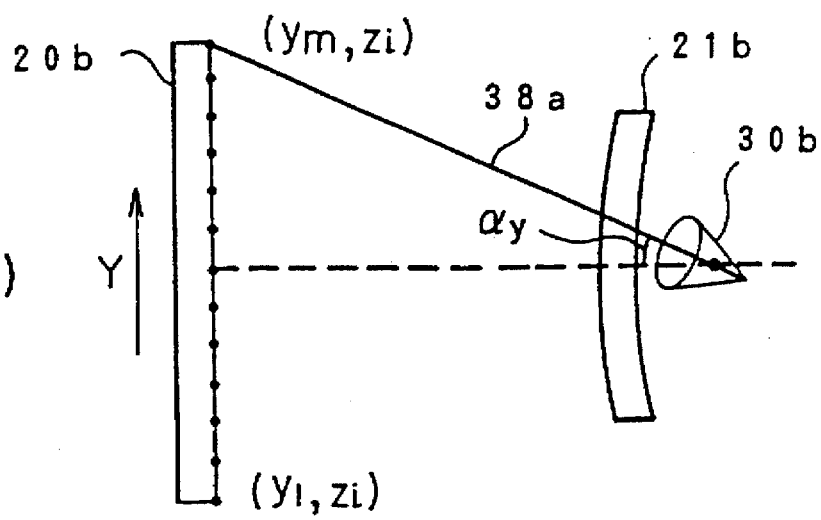
FIGS. 14(A), 14(B), and 14(C) are diagrams showing the manner in which an ocular optical system varies when seeing the light source display screen.
Figure 14:
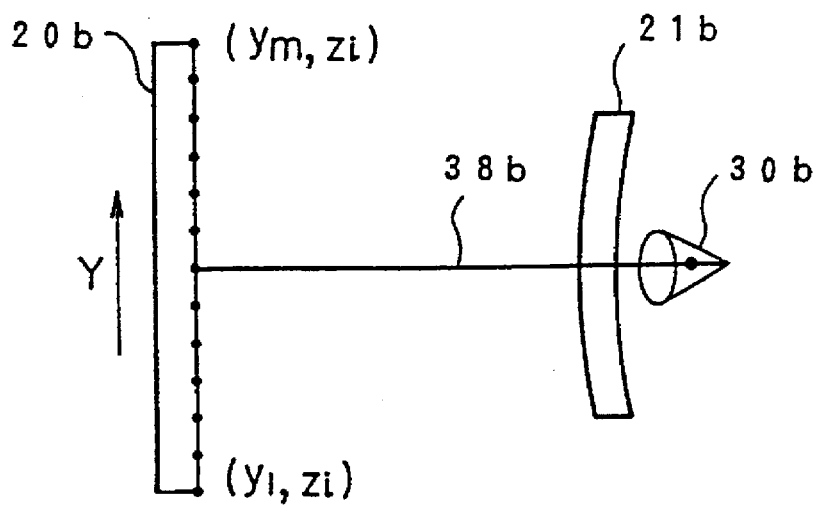
Figure 14:
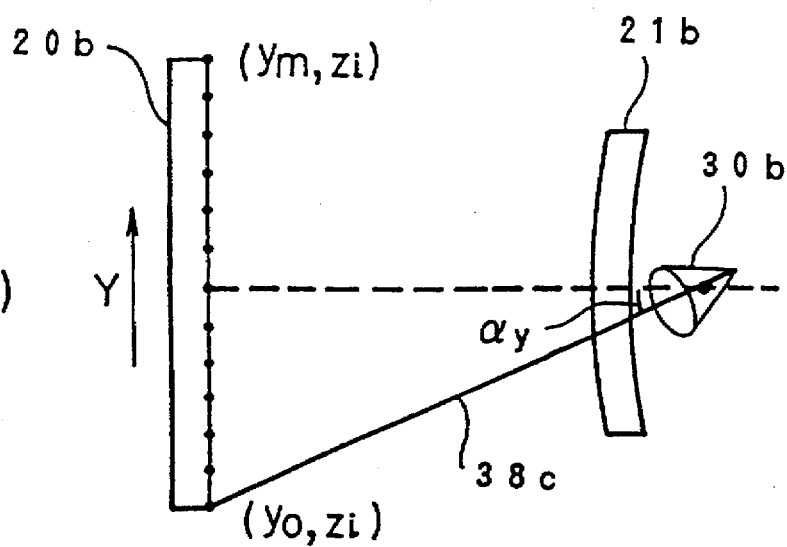

FIGS. 14(A), 14(B), and 14(C) show the manner in which the ocular optical system of the human eye 30b varies when seeing the light source display screen 20b. In FIGS. 14(A), 14(B), and 14(C), the angle through the human eye 30b is turned in the direction of the Z-axis is constant, and the angle through the human eye 30b is turned in the direction of the Y-axis is varied.

FIG. 14(A) shows the ocular optical system at the time the human eye 30b views an upper end of the light source display screen 20b. The human eye 30b is turned upwardly and directly faces a view dot ($y_m$, $z_i$) at the upper end of the light source display screen 20b. Therefore, a ray 38a of light from the upper end of the light source display screen 20b is applied obliquely downwardly to an eyeglass lens 21b positioned in front of the human eye 30b. The ray 38a of light which has passed through the eyeglass lens 21b enters the human eye 30b, forming an image on the retina thereof which is visually perceived. The human eye 30b is then turned in a negative direction of the Y-axis.

FIG. 14(B) shows the ocular optical system at the time the human eye 30b views the center of the light source display screen 20b. The human eye 30b is not turned and directly faces the center of the light source display screen 20b. A ray 38b of light from the center of the light source display screen 20b is applied perpendicularly to the eyeglass lens 21b. The ray 38b of light which has passed through the eyeglass lens 21b enters the human eye 30b, forming an image on the retina thereof which is visually perceived. The human eye 30b is further turned in the negative direction of the Y-axis.

FIG. 14(C) shows the ocular optical system at the time the human eye 30b views a lower end of the light source display screen 20b. The human eye 30b is turned downwardly and directly faces a view dot ($y_o$, $z_i$) at the lower end of the light source display screen 20b. Therefore, a ray 38c of light from the lower end of the light source display screen 20b is applied obliquely upwardly to the eyeglass lens 21b. The ray 38c of light which has passed through the eyeglass lens 21b enters the human eye 30b, forming an image on the retina thereof which is visually perceived.

In this manner, optical system data at all the view dots are generated when the human eye 30b is turned in the direction of the Y-axis. When the human eye 30b is turned, the values of various data vary. For example, the distance from the eyeglass lens to the cornea varies as the human eye 30b is turned. If the eyeglass lens is a multifocal lens, then the radii of curvature of concave and convex surfaces of the lens also vary as the position where the light is applied to the lens varies.

The angle formed between the rays 38a, 38c of light from the light source display screen and the X-axis is strictly not the same as the angle $\alpha_y$ because the direction of light varies when it passes through the eyeglass lens 21b.

In FIGS. 14(A) through 14(C), the human eye 30b is turned vertically in the direction of the Y-axis while the angle through which the human eye 30b is turned in the direction of the Z-axis on the light source display screen remains constant. However, optical system data corresponding to all the view dots are generated when the human eye 30b is also turned in the direction of the Z-axis, scanning the view dots from $z_i$ to $z_n$, as well as in the direction of the Y-axis. Based on the optical system data thus generated, the PSF calculating means determine PSFs with respect to the respective view dots, thus producing m×n PSFs.

The scenery image calculating means effect convolutional integration on image data displayed on the light source display screen with the PSFs according to the equation (5), thereby generating scenery image data 303 (see FIG. 11). The generated scenery image data are representative of successive images which are formed on the retina when the person wearing the eyeglasses turns his eyes to look around.

In this manner, images that would be visually perceived by a human being when his eyes are turned to look around can be simulated. Even if the eyeglass lens is a multifocal lens, it is possible to gain an objective recognition of the characteristics of the lens. As a consequence, the user of eyeglasses can easily select an eyeglass lens which best matches his eyes. For designing or evaluating a complex optical lens such as a progressive multifocal lens, optical system data of such an optical lens may be entered to accurately understand the characteristics of the lens.

While the light source display screen is assumed to be of a flat surface positioned at an infinitely far distance in the above embodiment, the light source display screen may be positioned closely to the ocular optical system. If the light source display screen is positioned closely to the ocular optical system, then the ocular optical system is simulated on the assumption that rays of light emitted from the ocular optical system are dispersed.

In the above embodiment, only one scenery image is displayed on the display unit. However, a plurality of scenery images generated using optical system data of a plurality of optical lenses having different specifications may be displayed simultaneously on the display screen of the display unit.

Figure 15:
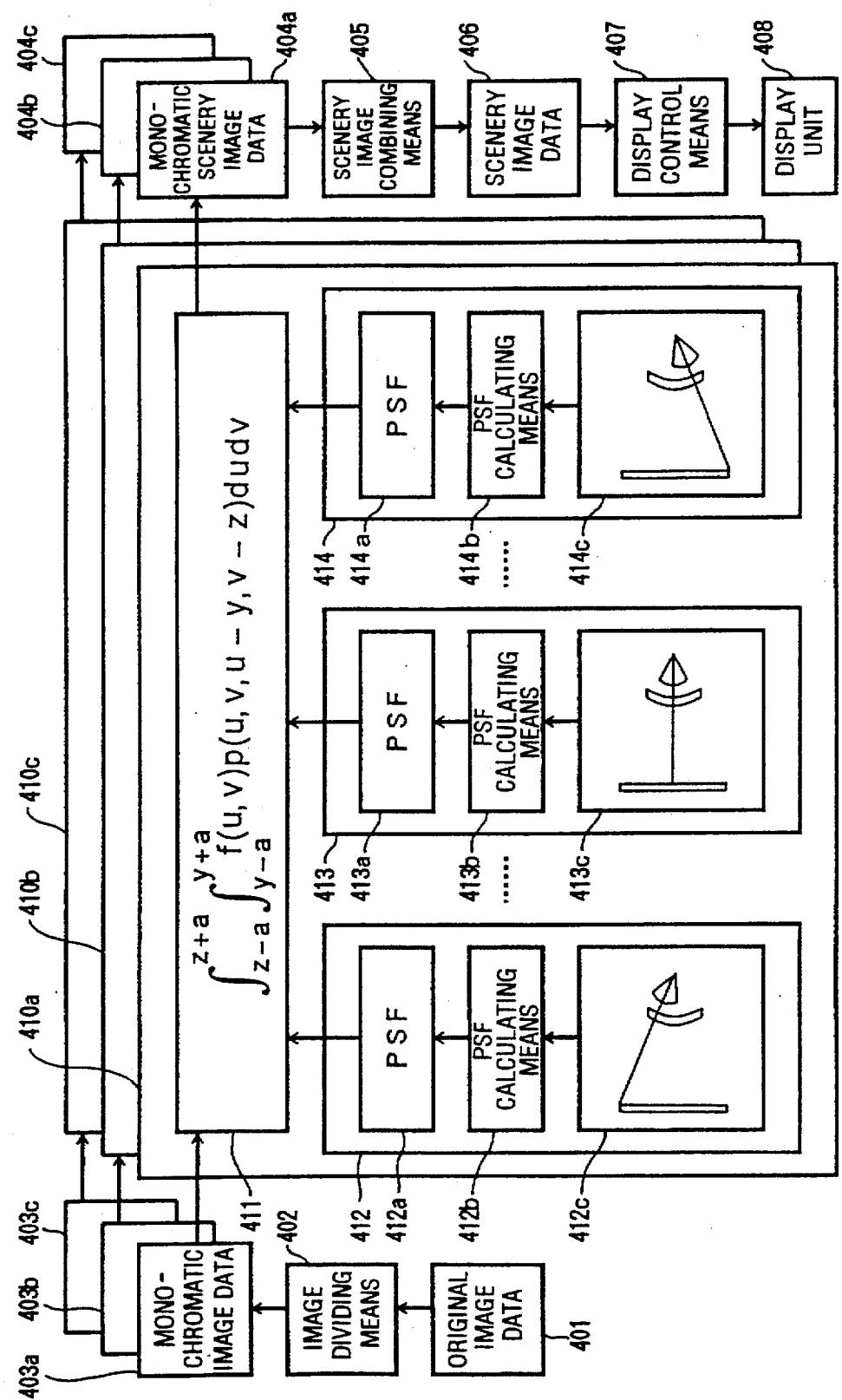
FIG. 15 is a block diagram showing the principles of an apparatus for simulating an ocular optical system, including means for processing data depending on chromatic aberration and the turning of a human eye taken.

FIG. 15 shows in block form the principles of an apparatus for simulating an ocular optical system, including means for processing data depending on chromatic aberration and the turning of a human eye taken. The simulating apparatus shown in FIG. 15 includes a light source display screen which is so large that the user cannot view the light source display screen in its entirety unless he turns his eye. The light source display screen displays a matrix of view dots.

Original image data 401 are generated which are representative of an original image displayed on the light source display screen. The original image data 401 are supplied to image dividing means 402. The image dividing means 402 spectrally divides the supplied original image data 401 into a plurality of monochromatic image data 403a–403c of respective wavelengths. Each of the monochromatic image data 403a–403c is image data produced when only the spectrum of a certain wavelength is extracted from the original image data 401. Specifically, the original image data 401 are divided into plural image data as respective spectral components at all predetermined wavelengths, and those image data are produced as the monochromatic image data 403a–403c of the predetermined wavelengths. The predetermined wavelengths may be established as desired, and may, for example, be wavelengths spaced at several nm in the wavelength range of visible light.

If the original image data 401 are of single-color data such as black-and-white image data, then the images obtained from the respective spectral components of the original image data 401 are identical in shape to each other. In this case, the original image data 401 may not be spectrally divided, but may be regarded directly as the monochromatic image data 403a–403c of the predetermined wavelengths. Therefore, the image dividing means 402 may be dispensed with.

The simulating apparatus also has a plurality of scenery image generators 410a–410c for processing the monochromatic image data 403a–403c, respectively. The scenery image generator 410a has PSF calculating units 412–414 associated with the respective view dots on the light source display screen. For example, if the light source display screen can be divided into a vertical array of m pixels or view dots and a horizontal array of n pixels or view dots, i.e., a matrix of m×n pixels or view dots, then the simulating apparatus has m×n PSF calculating units.

The PSF calculating units 412–414 contain optical system data 412c, 413c, 414c, respectively, which are generated when the user has turned his eye in order to focus the images of the corresponding view dots on the retina. The optical system data 412c, 413c, 414c include positional data of the corresponding view dots, data of an optical lens including curvatures of convex and concave surfaces thereof, a refractive index thereof, and data of a human eye including a cornea, a pupil, a lens, a retina, and the angle through which the human eye is turned. The data of the optical lens can be determined by corresponding design values of the lens. The data of the human eye are basically determined using the Gullstrand's eye model, with the ocular axis length being determined depending on the visual power of the user of the optical lens. The refractive index of each of the mediums of the ocular optical system is a refractive index with respect to light of a certain wavelength which is applied thereto.

The PSF calculating units 412–414 have respective PSF calculating means 412b, 413b, 414b for determining PSFs 412a, 413a, 414a, respectively, based on the optical system data 412c, 413c, 414c. Each of the PSFs 412a, 413a, 414a is a function representing a distribution on an image plane of light emitted from a certain view dot. The scenery image generator 410a also has scenery image calculating means 411 for effecting convolutional integration on the corresponding monochromatic image data 403a with the PSFs 412a, 413a, 414a, thereby generating monochromatic scenery image data 404a.

The other scenery image generators 410b, 410c are identical to the scenery image generator 410a, and similarly generate monochromatic scenery image data 404b, 404c, respectively, based on the optical system data at the corresponding wavelengths.

The simulating apparatus also has scenery image combining means 405 for combining the monochromatic scenery image data 404a–404c into scenery image data 406. The simulating apparatus further includes display control means 407 for displaying an image represented by the scenery image data 406 on a display unit 408. The display unit 408 now displays on its display screen an overall scenery image, containing effects of chromatic aberration, that can be visually recognized by the user when he moves the eye vertically and horizontally.

A simulating process carried out by the simulating apparatus shown in FIG. 15 will be described in greater detail below.

Original image data to be displayed for simulation are generated. The original image data are displayed on the light source display screen in a range which can be focused when the user turns his eye.

The original image data are generated for displaying an image on the light source display screen 20b shown in FIG. 12.

The original image data are spectrally divided into monochromatic image data of predetermined wavelengths, which may be represented by three spectral lines of a d-line (He), an F-line (H), and a C-line (H) or an e-line, an F'-line, and a C'-line. The original image data may be spectrally divided into monochromatic image data of more wavelengths including the above wavelengths, or into monochromatic image data at intervals of 5 nm in a wavelength range from 380 nm to 780 nm.

Optical system data to be used when the light source display screen is viewed while the user is turning his eye are generated with respect to the wavelengths. To generate the optical system data, it is necessary to know refractive indexes of the eyeglass lens at the respective wavelengths.

The refractive index of an optical lens is determined by the material thereof. Generally, the characteristics of a lens are indicated by the Abbe number which is the reciprocal of the dispersive power. There are two types of Abbe numbers, i.e., an Abbe number with respect to the d-line and an Abbe number with respect to the e-line. While Abbe number with respect to the e-line is slightly smaller than the Abbe number with respect to the d-line, they equally signify the degree of dispersion.

The smaller the Abbe number, the greater the degree to which the refractive index varies depending on the wavelength of light. Stated otherwise, eyeglass lenses that are manufactured and sold have a smaller chromatic aberration at their marginal edge, i.e., smaller color fringes, if the Abbe number indicated on them is greater. In general, an optical material is preferable for use as eyeglass lens if its Abbe number is 40 or greater (with respect to the d-line). If the degree of an eyeglass lens is 1/10 or more of the Abbe number, then the eyeglass lens suffers significant chromatic aberration.

The refractive index of an optical lens to be simulated at any desired wavelength can be calculated from the Abbe number. Using the refractive indexes at the respective wavelengths, optical system data to be used when the view dots on the light source display screen are viewed while the user is turning his eye are generated. The optical system data are generated in the same manner as described above with reference to FIGS. 14(A) through 14(C).

Then, various data are established for the ocular optical system with the eye being turned as shown in FIG. 7. The data relative to the eyeglass lens 21a include radii of curvature of convex and concave surfaces thereof and a refractive index thereof. The data relative to the human eye 30a include radii of curvature of various surfaces of the cornea and the lens, and refractive indexes of the cornea 31a, the lens 33a, and the vitreous humor 34a. The refractive indexes relative to the human eye 30a are determined using the Gullstrand's eye model, and the refractive index of the eyeglass lens 21a is determined by actual measurements. The distances between the cornea 31a, the pupil 32a, the lens 33a, and the retina 35a are established. The data relative to the human eye are basically determined using data of the Gullstrand's eye model, and the distance up to the retina from the cornea or the curvature of the convex surface of the cornea is established depending on the visual power of the human eye to be simulated.

Thereafter, the positions of the view dots on the light source display screen are established. By tracking the rays of light from the positions of the view dots, it is possible to determine the angle θ formed between the ray 36a of light applied to the eyeglass lens 21a and the reference axis 37a and the angle α through which the eye is turned.

The optical system data at a desired wavelength can thus be determined as described above. The optical system data are determined at all predetermined wavelengths. In this manner, the optical system data with the human eye directed to any optional view dot can be determined at all view dots with respect to the predetermined wavelengths.

The monochromatic image data are subjected to convolutional integration with the PSFs calculated at the corresponding wavelengths, thereby producing monochromatic scenery image data. If it is assumed that a light intensity distribution of an ideal image on the image plane is represented by $f(y, z)$ and a PSF at a point $(y, z)$ by $p(x, y, u, v)$, then the light intensity at the point $(y, z)$ on the retina is expressed by the above equation (5). Using the equation (5), the light intensities at points on the retina are determined with respect to each of the angles through which the eye is turned, for thereby determining monochromatic scenery image data. The monochromatic scenery image data are generated at all wavelengths.

All the generated monochromatic scenery image data are combined with each other. In an RGB trichromatic system which employs the color matching functions, the value of a stimulus applied to photoreceptors at the time light at a certain wavelength reaches the retina is indicated by the intensities of three spectral lines, i.e., R (700 nm), G (546.3 nm), and B (435.8 nm). Stated otherwise, the color matching functions make it possible to specify the intensities of lights R, G, B for replacing light in any optional color with three lights R, G, B to enable the human eye to sense the color.

If the original image is divided into images of three colors, then the images are regarded as having colors at the three spectral lines R (700 nm), G (546.3 nm), and B (435.8 nm). For example, if the original image is divided into three colors of the d-line, the F-line, and the C-line, the d-line, the F-line, and the C-line are regarded as spectral lines for G, B, R. If the original image is divided into three colors of the e-line, the F'-line, and the C'-line, the e-line, the F'-line, and the C'-line are regarded as spectral lines for G, B, R. In this manner, when the image is to be displayed on the display unit, the three colors can correspond to the R, G, B dots, respectively, of a CRT (Cathode-Ray Tube).

The generated scenery image data are representative of successive images which are formed on the retina when the person wearing the eyeglasses turn his eyes to look around. The displayed images contain effects of chromatic aberration of the eyeglass lens.

In this fashion, images that would be visually perceived by a human being when his eyes are turned to look around can be simulated, with effects of chromatic aberration being included. Even if the eyeglass lens is a multifocal lens, it is possible to gain an objective recognition of the characteristics of the lens including effects of chromatic aberration. As a consequence, the user of eyeglasses can easily select an eyeglass lens which best matches his eyes. For designing or evaluating a complex optical lens such as a progressive multifocal lens, optical system data of such an optical lens may be entered to accurately understand the characteristics of the lens.

Figure 16:
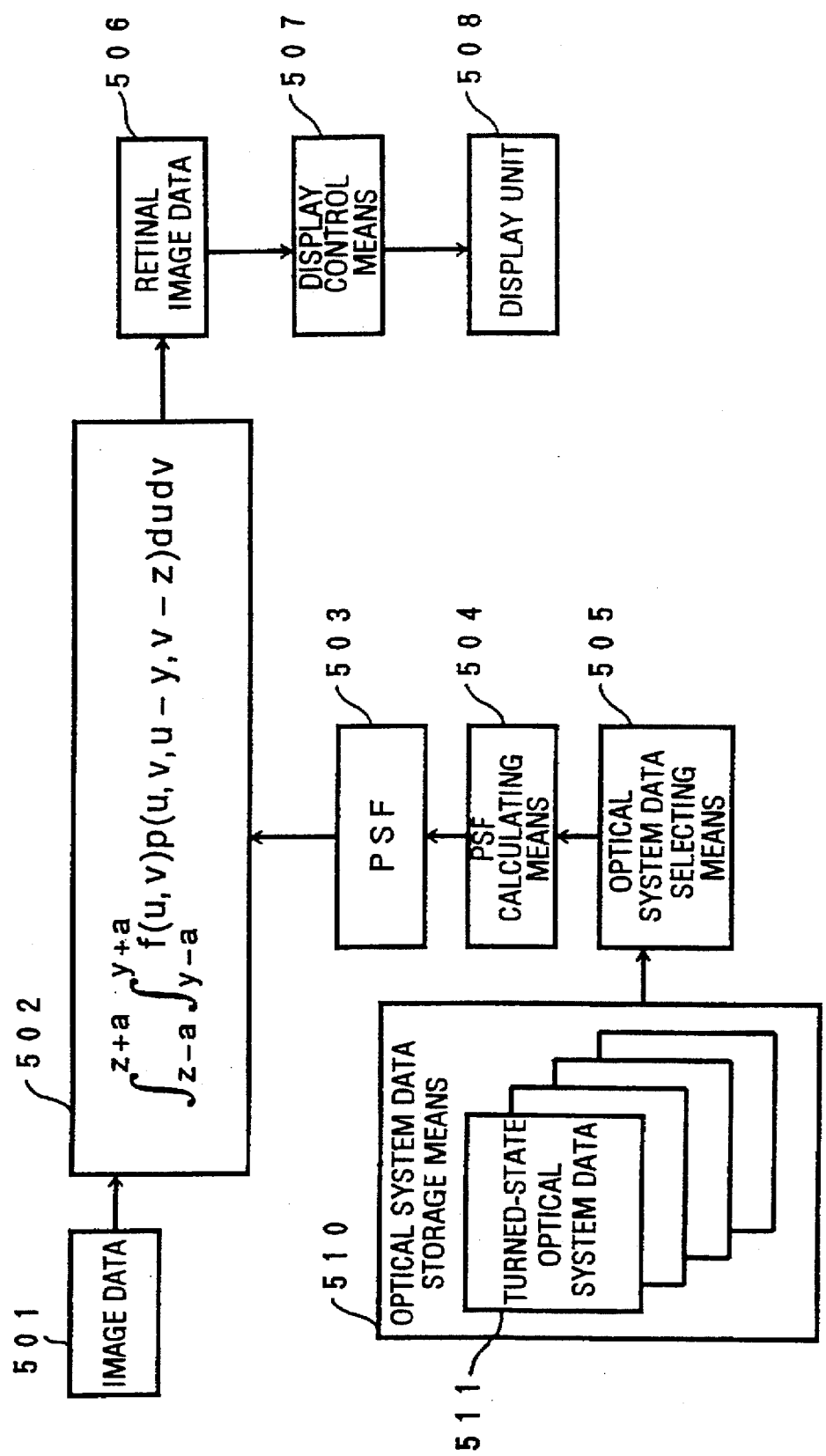
FIG. 16 is a block diagram showing the principles of an apparatus for simulating an ocular optical system, including means for processing data depending on the angle through which a human eye is turned.

FIG. 16 shows in block form the principles of an apparatus for simulating an ocular optical system, including means for processing data depending on the angle through which a human eye is turned.

As shown in FIG. 16, a plurality of turned-state optical system data 511 at respective angles through which the human eye is turned are stored in optical system data storage means 510. The turned-state optical system data 511 include data relative to the position of a light source display screen, optical data relative to an optical lens, and optical data relative to the human eye, including the angles through which the human eye is turned, a cornea, a pupil, and a retina thereof.

The optical data relative to the optical lens are determined based on design values of the lens used. The optical data relative to the human eye are basically determined using the Gullstrand's eye model, with the ocular axis length or the curvature of the convex surface of the cornea being determined depending on the visual power of the user of the optical lens. Furthermore, measursable data can be measured directly from the user for whom the apparatus for simulating an ocular optical system is used.

The data relative to the position of the light source display screen are established depending on the angle through which the human eye is turned. Specifically, the distance from the human eye to the light source display screen is set to a distance at which an image displayed on the light source display screen is focused on the retina. If the optical lens is a multifocal lens, this distance varies depending on the angle through which the human eye is turned. For example, if the optical lens is a multifocal lens having a central distant-vision portion and a lower near-vision portion, then the light source display screen is positioned at an infinitely far distance when the human eye is not turned, and positioned at a distance of several tens of centimeters from the human eye when the human eye is turned downwardly.

When an angle, to be simulated, through which the human eye is turned is indicated by an inputting operation of the operator, optical system data selecting means 505 selects one of the turned-state optical system data 511 corresponding to the indicated angle from the optical system data storage means 510. PSF calculating means 504 determines a PSF 503 based on the selected turned-state optical system data 511. The PSF 503 is a function representing a distribution on an image plane of light emitted from a certain point.

Optional image data 501 representative of an image to be displayed on the light source display screen are generated. Retinal image calculating means 502 effects convolutional integration on the image data 501 with the PSF 503, determining retinal image data 506. The image data 501 comprise digital image data of a visual mark such as Randolt rings or the like. The retinal image data 506 are converted by display control means 507 into display data, which are supplied to a display unit 508 to display a retinal image based on the supplied display data.

The retinal image displayed on the display unit 508 comprises an image that would be actually formed on the retina of a human eye, and hence provides an accurate objective indication of how the image is seen. By selecting an angle through which the human eye is turned, a retinal image at the selected angle can be displayed on the display unit 508.

The distance up to a light source display screen that is established for simulating a retinal image with respect to a bifocal lens which has a central distant-vision portion and a lower near-vision portion will be described below.

Figure 17:
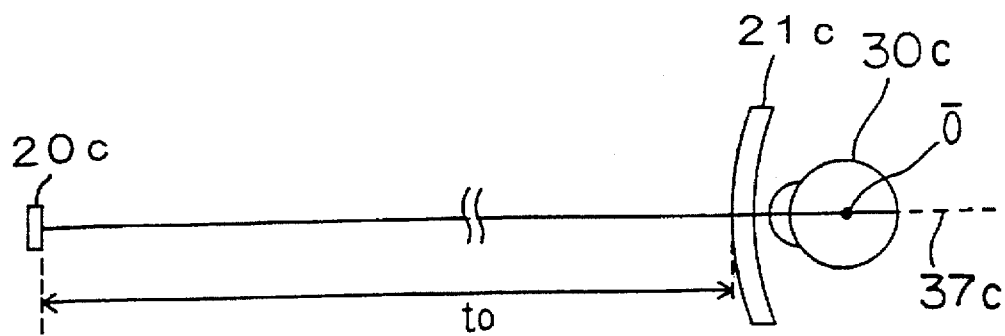
FIG. 17(A) is a schematic diagram showing the positional relationship between a human eye and a light source display screen when the human eye is not turned.
FIG. 17(B) is a schematic diagram showing the positional relationship between a human eye and a light source display screen when the human eye is turned downwardly.
Figure 17:
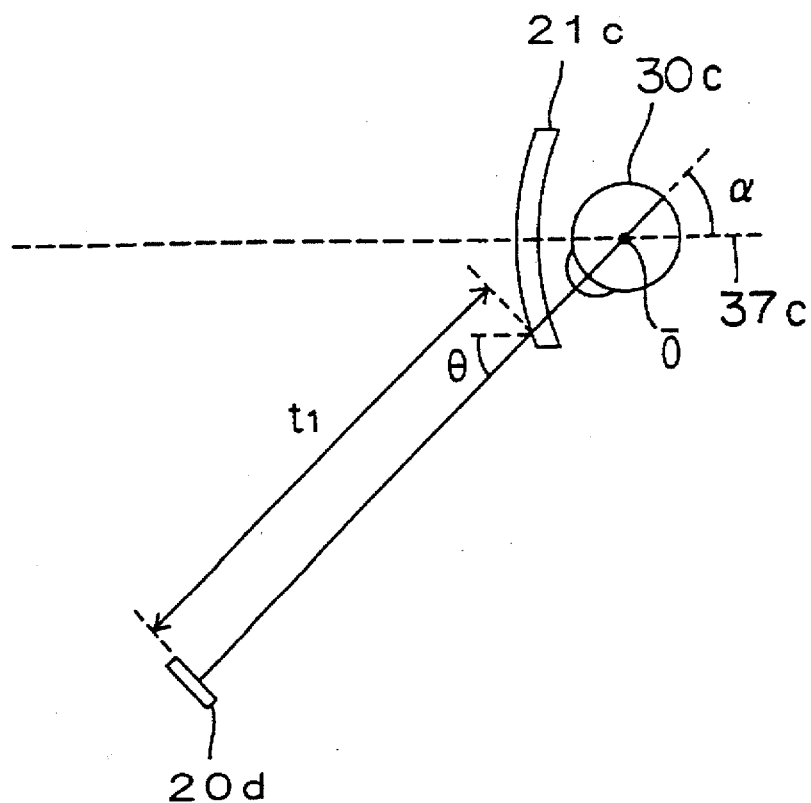

FIGS. 17(A) and 17(B) show the positional relationship between a human eye and a light source display screen when the human eye is not turned and is turned. In FIGS. 17(A) and 17(B), a straight reference axis 37c extends through the center of an eyeglass lens 21c and the center O about which a human eye 30c is turned through an angle α between the reference axis 37c and a straight line that extends through the center O and the center of the cornea. The optical lens 21c has a central distant-vision portion and a lower near-vision portion.

FIG. 17(A) shows the human eye 30c as it is not turned. The human eye 30c views a light source display screen 20c through the central distant-vision portion of the optical lens 21c. The distance to between the light source display screen 20c and the optical lens 21c is infinitely large. By effecting light ray tracking in this position, turned-state optical system data can be obtained when the human eye 30c is not turned.

FIG. 17(B) shows the human eye 30c as it is turned downwardly through an angle α. The human eye 30c views the light source display screen 20d through the lower near-vision portion of the optical lens 21c. The distance $t_1$ between the light source display screen 20c and the optical lens 21c is about several tens of centimeters. By effecting light ray tracking in this position, turned-state optical system data can be obtained when the human eye 30c is turned through the angle α.

A number of such turned-state optical system data are produced at slightly different angles α. While the human eye 30c is turned vertically in FIGS. 17(A) and 17(B), turned-state optical system data may be generated when the human eye 30c is turned both vertically and horizontally. These turned-state optical system data are stored in the optical system data storage means 510 (see FIG. 16).

The angle θ formed between the direction in which the light is applied from the light source display screen 20d to the optical lens 21c and the reference axis 37c is not the same as the angle G because the light is diffracted and changes its course of travel when it passes through the optical lens 21c.

When one of the turned-state optical system data is selected and a PSF is generated therefrom, a PSF is determined at any optional angle at which the human eye is turned.

The retinal image calculating means effects convolutional integration on image data displayed on the light source display screen with the PSF, thereby generating retinal image data. If it is assumed that a light intensity distribution of an ideal image on the image plane is represented by f(y, z) and a PSF at a point (y, z) by p (x, y, u, v), then the light intensity at the point (y, z) on the retina is expressed by the above equation (5).

The retinal image data thus generated are supplied to the display control means, which displays a retinal image on the display unit. Thus, a retinal image produced when the optical lens would be worn can be simulated at a selected angle through which the human eye is turned. The image data to be simulated are established at a distance for focusing a corresponding image at the retina at all times even if the optical lens is a multifocal lens. Consequently, images that would be seen through a multifocal lens as the eye shifts its view point from distant vision to near vision can be simulated.

In FIG. 16, a plurality of turned-state optical system data are stored in advance in the optical system data storage means. However, turned-state optical system data may be calculated from optical system data produced when the human eye is not turned.

Figure 18:
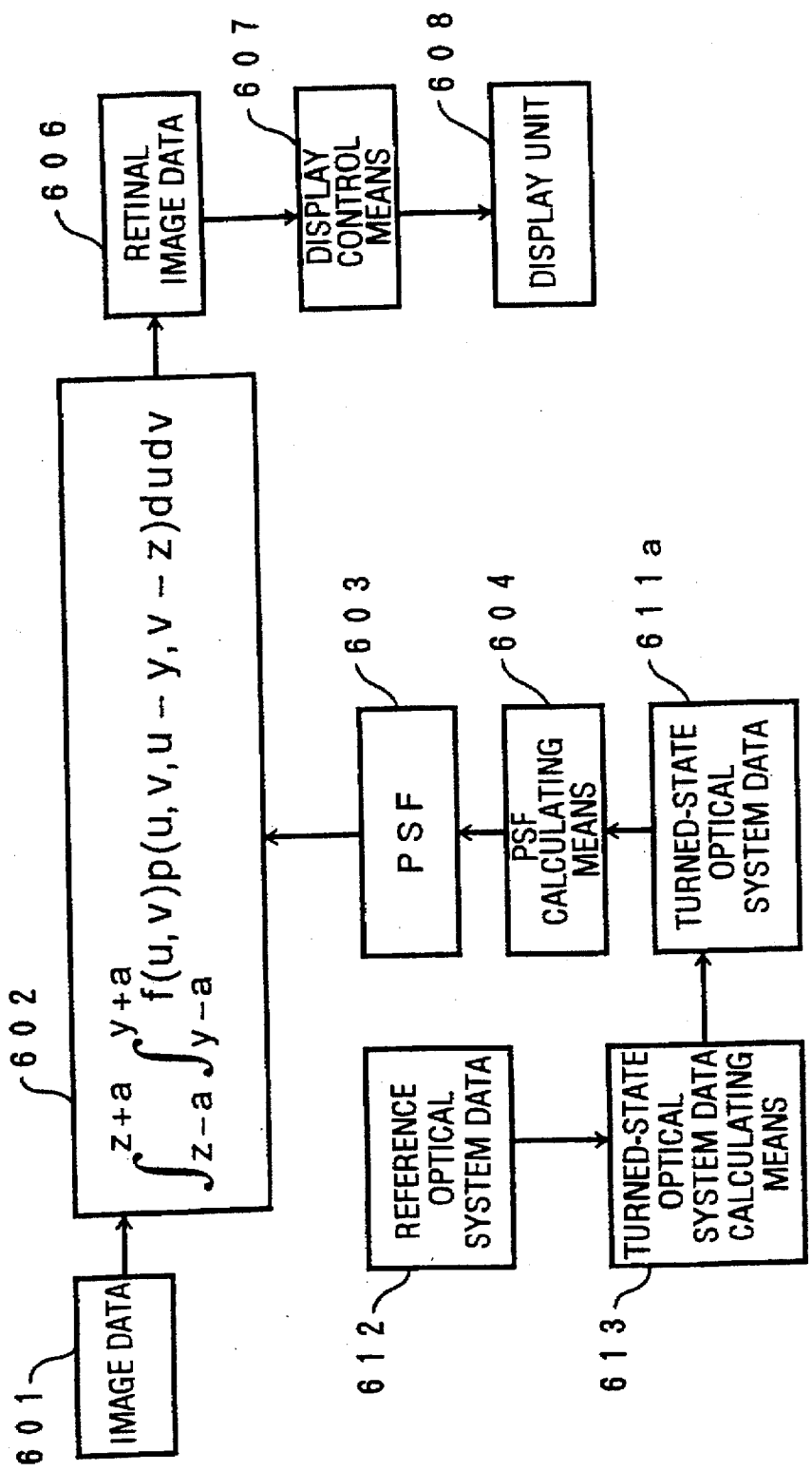
FIG. 18 is a block diagram showing the principles of another apparatus for simulating an ocular optical system, including means for processing data depending on the angle through which a human eye is turned.

FIG. 18 shows in block form the principles of another apparatus for simulating an ocular optical system, including means for processing data depending on the angle through which a human eye is turned.

As shown in FIG. 18, reference optical system data 612 produced when the human eye is not turned are established. The reference optical system data 612 include data relative to the position of a light source display screen disposed on an extension of a reference line, optical data relative to an optical lens, and optical data relative to the human eye, including a cornea, a pupil, and a retina thereof.

The optical data relative to the optical lens are determined based on design values of the lens used. The optical data relative to the human eye are basically determined using the Gullstrand's eye model, with the ocular axis length or the curvature of the convex surface of the cornea being determined depending on the visual power of the user of the optical lens. Furthermore, measurable data can be measured directly from the user for whom the apparatus for simulating an ocular optical system is used.

Based on the reference optical system data 612, turned-state optical system data calculating means 613 calculates turned-state optical system data 611a at any optional angle through which the human eye is turned. PSF calculating means 604 determines a PSF 603 based on the calculated turned-state optical system data 611a.

Image data 601 representative of an image to be displayed on the light source display screen are generated. Retinal image calculating means 602 effects convolutional integration on the image data 601 with the PSF 603, determining retinal image data 606. The image data 601 comprise digital image data of a visual mark such as Randolt rings or the like. The retinal image data 606 are converted by display control means 607 into display data, which are supplied to a display unit 608 to display a retinal image based on the supplied display data. The retinal image displayed on the display unit 608 comprises an image that would actually formed on the retina of a human eye, and hence provides an accurate objective indication of how the image is seen. The turned-state optical system data calculating means 613 can select an angle, to be simulated, through which the human eye is turned, and a retinal image of image data established at a distance corresponding to the selected angle is displayed on the display unit 608.

A retinal image which is simulated for the use of monofocal eyeglasses by the simulating apparatus will specifically be described below. In the simulation, the eyeglass lens has a refractive index of 1.50 and a degree of −6.00, and the human eye is turned through 15° and 30°.

Figure 19:
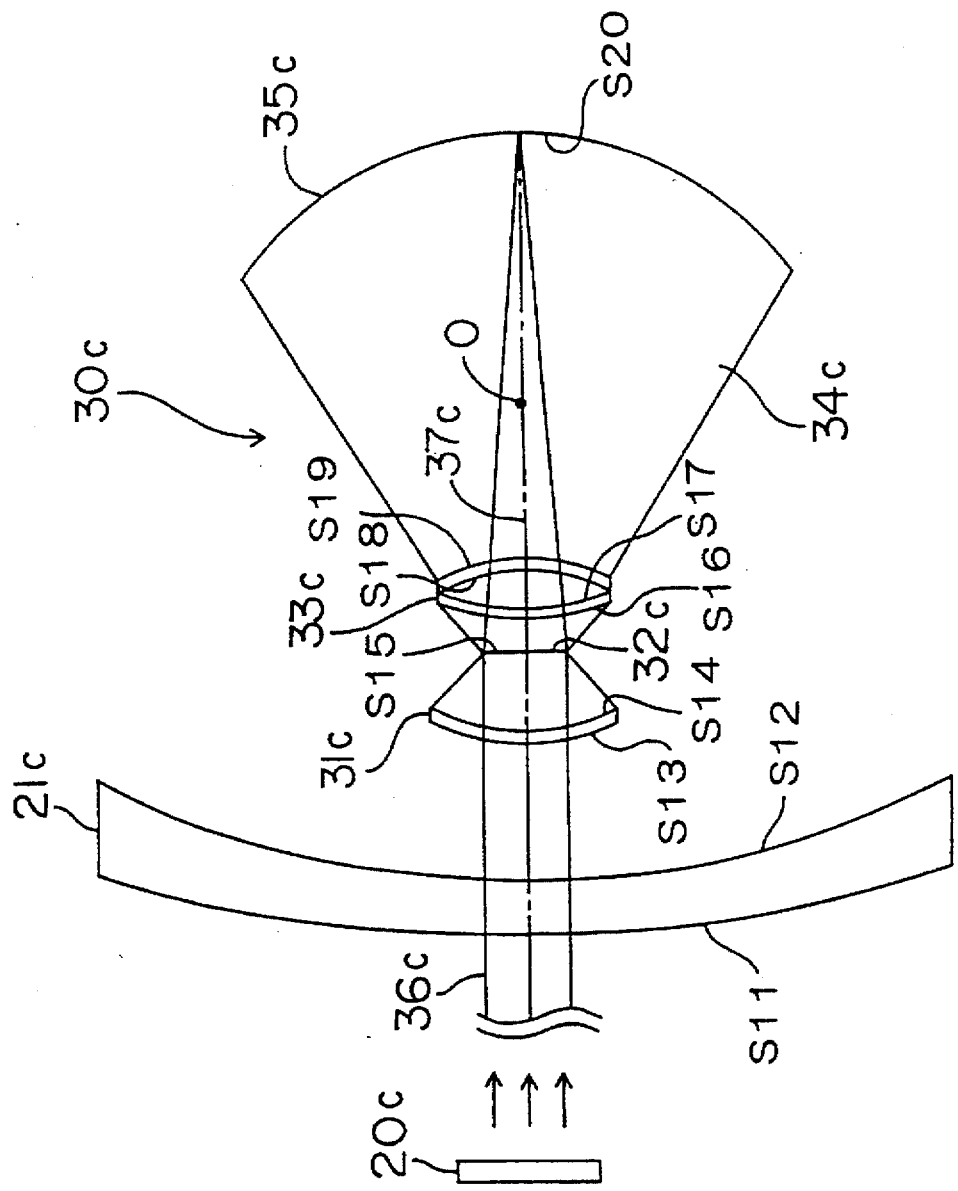
FIG. 19 is a schematic diagram of an ocular optical system for obtaining reference optical system data.

FIG. 19 shows an ocular optical system for obtaining reference optical system data. In FIG. 19, a ray 36c of light emitted from a light source display screen 20c which displays an image based on image data passes through an eyeglass lens 21c and enters a human eye 30c. The human eye 30c directly faces the light source display screen 20c, and has a cornea 31c on its front. The human eye 30c also has a pupil 32c positioned behind the cornea 31c for restricting the amount of light entering the human eye 30c, a lens 33c positioned behind the pupil 32c, a vitreous humor 34c positioned behind the lens 33c, and a retina 35c positioned behind the vitreous humor 34c. The human being detects light that has entered the human eye 30c and recognizes an image produced by the light through the retina 35c.

Reference optical system data of light entering the human eye 30c are generated based on the above ocular optical system. The distance of the light source display screen 20c from the human eye 30c is assumed to be infinitely far, and hence parallel rays of light from the light source display screen 20c enter the eyeglass lens 21c.

The eyeglass lens 21c comprises a lens having a refractive index of 1.50 and a degree of −6.00. The eyeglass lens 21c has a front convex surface and a rear concave surface. The radii of curvature of these front convex and rear concave surfaces of the eyeglass lens 21c, and the thickness of the eyeglass lens 21c are equal to corresponding design values of a lens to be simulated. A distance from the eyeglass lens 21c up to the cornea 31c is established.

Optical data relative to the human eye 30c are basically generated using the Gullstrand's eye model. However, since the ocular optical system is simulated for vision corrected by eyeglasses with the degree of −6.00, the human eye 30c needs to be near-sighted. Therefore, only the ocular axis length of the human eye 30c is set to a value depending on the visual power of the user. In this manner, reference optical system data relative to the human eye 30c having any optional visual power are generated.

The ocular optical system shown in FIG. 19 has various surfaces associated with its components referred to above. Specifically, the eyeglass lens 21c has a front surface S11 and a rear surface S12. The cornea 31c has a front surface S13 and a rear surface S14. The pupil 32c has a pupil surface S15. The lens 33c has a first front surface S16, a first rear surface S17, a second front surface S18, and a second rear surface S19. The retina 35c has a retina surface S20. These surfaces S11–S20 have various data, as the generated reference optical system data, described in Table 2 shown below.

TABLE 2

| Medium/ Surface | Radius of Curvature | Effective Radius | Thickness | Refractive index for d-line | Thickness Subtotal |
| --- | --- | --- | --- | --- | --- |
| Air |  |  | 0.00000 | 1.00000 | 0.000 |
| S1 | 388.80249 | 37.500 |  |  |  |
| Eyeglass lens |  |  | 1.30000 | 1.50000 | 1.300 |
| S2 | 68.58711 | 37.500 |  |  |  |
| Air |  |  | 12.00000 | 1.00000 | 13.000 |
| S3 | 7.70000 | 5.000 |  |  |  |
| Cornea |  |  | 0.50000 | 1.37600 | 13.500 |
| S4 | 6.80000 | 5.000 |  |  |  |
| Anterior chamber |  |  | 2.50000 | 1.33600 | 16.000 |
| S5 | (planar) | 2.500 |  |  |  |
| Posterior chamber |  |  | 0.54600 | 1.38600 | 16.600 |
| S6 | 10.00000 | 3.800 |  |  |  |
| Lens |  |  | 0.54600 | 1.38600 | 17.146 |
| S7 | 7.91100 | 3.800 |  |  |  |
| Lens |  |  | 2.41900 | 1.40600 | 19.565 |
| S8 | −5.76000 | 3.800 |  |  |  |
| Lens |  |  | 0.63500 | 1.38600 | 20.200 |
| S9 | −6.00000 | 3.800 |  |  |  |
| Vitreous |  |  | 19.57135 | 1.33600 | 39.771 |
| S10 | −13.77135 | 10.000 |  |  |  |
| Retina |  |  | 0.00000 | 1.33600 | 39.771 |

In Table 2 above, the radii of curvature, the effective radii, the thicknesses, and the thickness subtotals are expressed in [mm]. Based on the above reference optical system data, turned-state optical system data are determined when the human eye is turned through an optional angle. For determining turned-state optical system data, the direction in which light is emitted from the light source display screen is fixed, and the position of the eyeglass lens is rotated about the center about which the human eye is turned, in a direction opposite to the direction in which the human eye is turned, in order to facilitate calculations.

Figure 20:
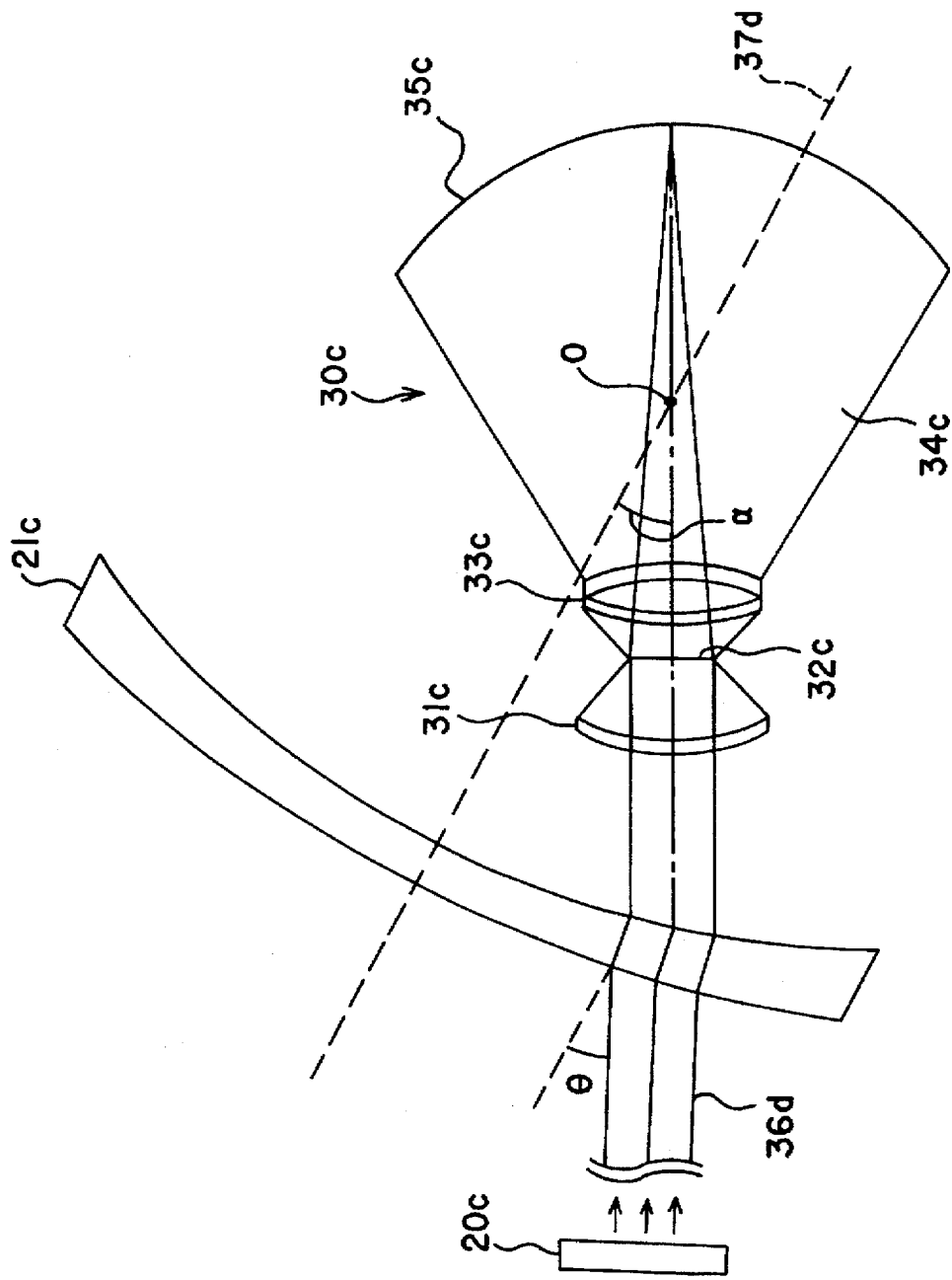
FIG. 20 is a schematic diagram of the ocular optical system which has been turned.

FIG. 20 shows an ocular optical system which has been turned downwardly. The light emitted from the light source display screen travels in a direction parallel to the X-axis, and the eyeglass lens is rotated about the center O about which the human eye is turned, in a direction opposite to the direction in which the human eye is turned.

In FIG. 20, a straight reference axis 37d extends through the center of an eyeglass lens 21c and the center O about which a human eye 30c is turned. A light source display screen 20c is positioned below the reference axis 37d. A ray 36d of light emitted from the light source display screen 20c passes obliquely through a lower portion of the eyeglass lens 21c and enters the human eye 30c. The human eye 30c is turned and directly faces the light source display screen 20c, and has a cornea 31c on its front. The human eye 30c also has a pupil 32c positioned behind the cornea 31c for restricting the amount of light entering the human eye 30c, a lens 33c positioned behind the pupil 32c, a vitreous humor 34c positioned behind the lens 33c, and a retina 35c positioned behind the vitreous humor 34c.

When the eyeglass lens 21c is rotated, the ray 36d of light from the light source display screen 20c is obliquely applied to the lower portion of the eyeglass lens 21c. Therefore, the direction of the light entering the eyeglass lens 21c and the direction of the light leaving the eyeglass lens 21c are slightly different from each other. Therefore, the angle θ formed between the ray 36d of light from the light source display screen 20c and the reference axis 37d, and the angle α through which the human eye 35c is turned are slightly different from each other. For example, if the eyeglass lens 21c is a negative-meniscus lens, then the angle α is smaller than the angle θ.

Turned-state optical system data when the human eye is turned through 15° and 30° can be calculated from the reference optical system data in Table 2. Based on the calculated turned-state optical system data, the PSF calculating means calculates a PSF. The PSF is then subjected to convolutional integration thereby to generate retinal image data.

Retinal images produced from image data representing the Randolt rings shown in FIG. 8 when the human eye is turned 15° and 30°, respectively, will be described below.

Figure 21:
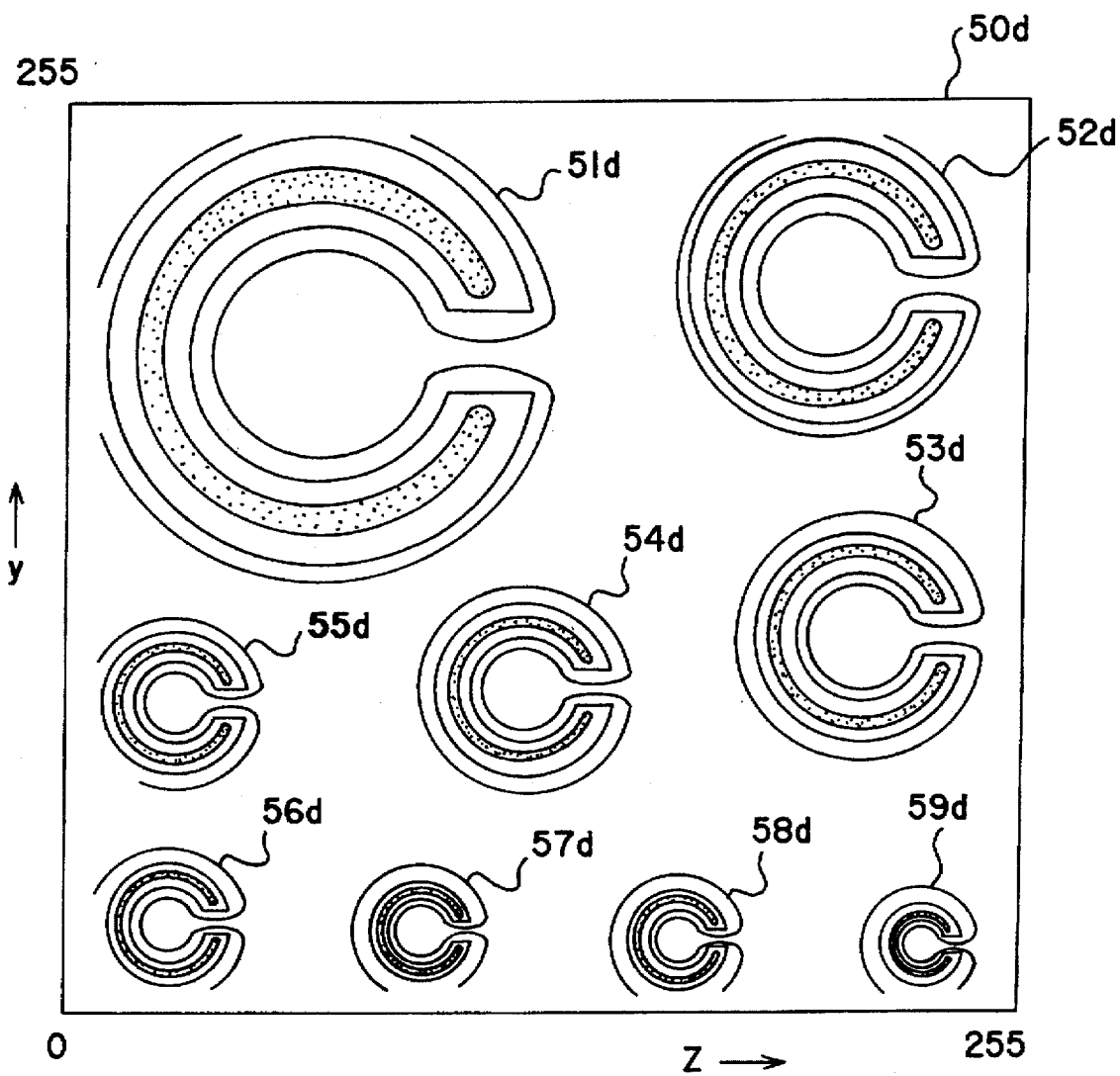
FIG. 21 is a view of a retinal image when the human eye is turned 15°.

FIG. 21 shows a retinal image 50d when the human eye is turned 15°. The retinal image 50d comprises retinal images 51d–59d corresponding respectively to the Randolt rings 41–49 shown in FIG. 8. Actually, the retinal images 51d–59d are viewed as blurred images having a continuously varying density. In FIG. 21, such a continuously varying density of each of the retinal images 51d–59d is expressed by contour lines such that the density is progressively greater toward the center of the retinal images, or progressively smaller toward the outer edge of the retinal images.

Figure 22:
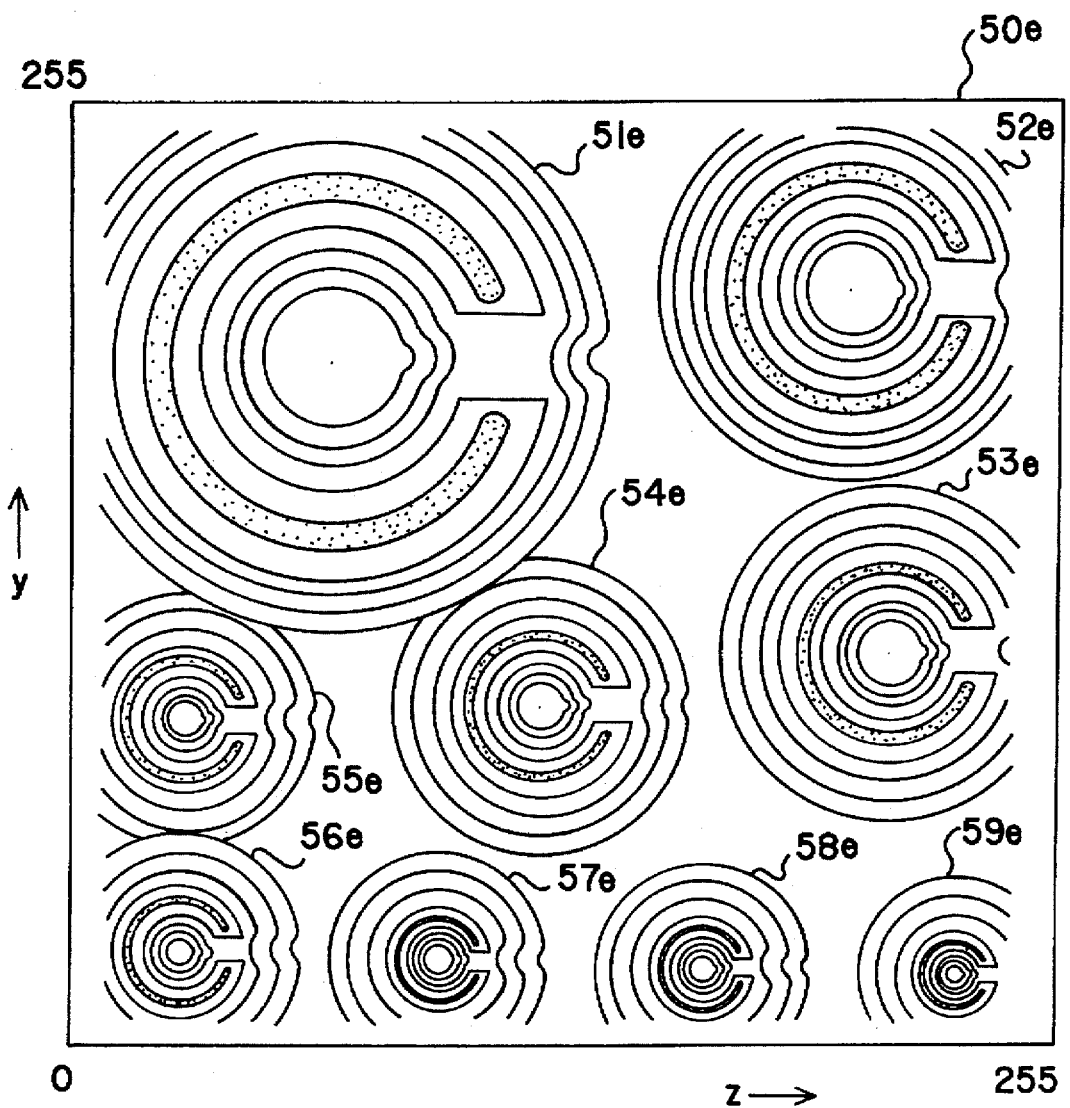
FIG. 22 is a view of a retinal image when the human eye is turned 30°.

FIG. 22 shows a retinal image 50e when the human eye is turned 30°. The retinal image 50e comprises retinal images 51e–59e corresponding respectively to the Randolt rings 41–49 shown in FIG. 8. Actually, the retinal images 51e–59e are viewed as blurred images having a continuously varying density. The retinal images 51e–59e are blurred to a greater extent than the retinal images 51d–59d which are produced when the human eye is turned 15°.

When retinal images at different angles through which the human eye is turned are simulated as described above, any changes in the manner in which the retinal image is seen due to changes in the angle through which the human eye is turned can objectively be recognized. This process is particularly effective for comparing images which would be seen through near- and distant-vision portions of a multifocal lens.

Monofocal and multifocal lenses make images look differently at their marginal edges though images look in the same manner in the central areas thereof. When images produced by these monofocal and multifocal lenses are simulated while the human eye is being turned, the difference between the manner in which images are seen through the monofocal and multifocal lenses can easily be perceived. Similarly, images produced by monofocal spherical and aspherical lenses can easily be compared with each other by simulation.

Figure 23:
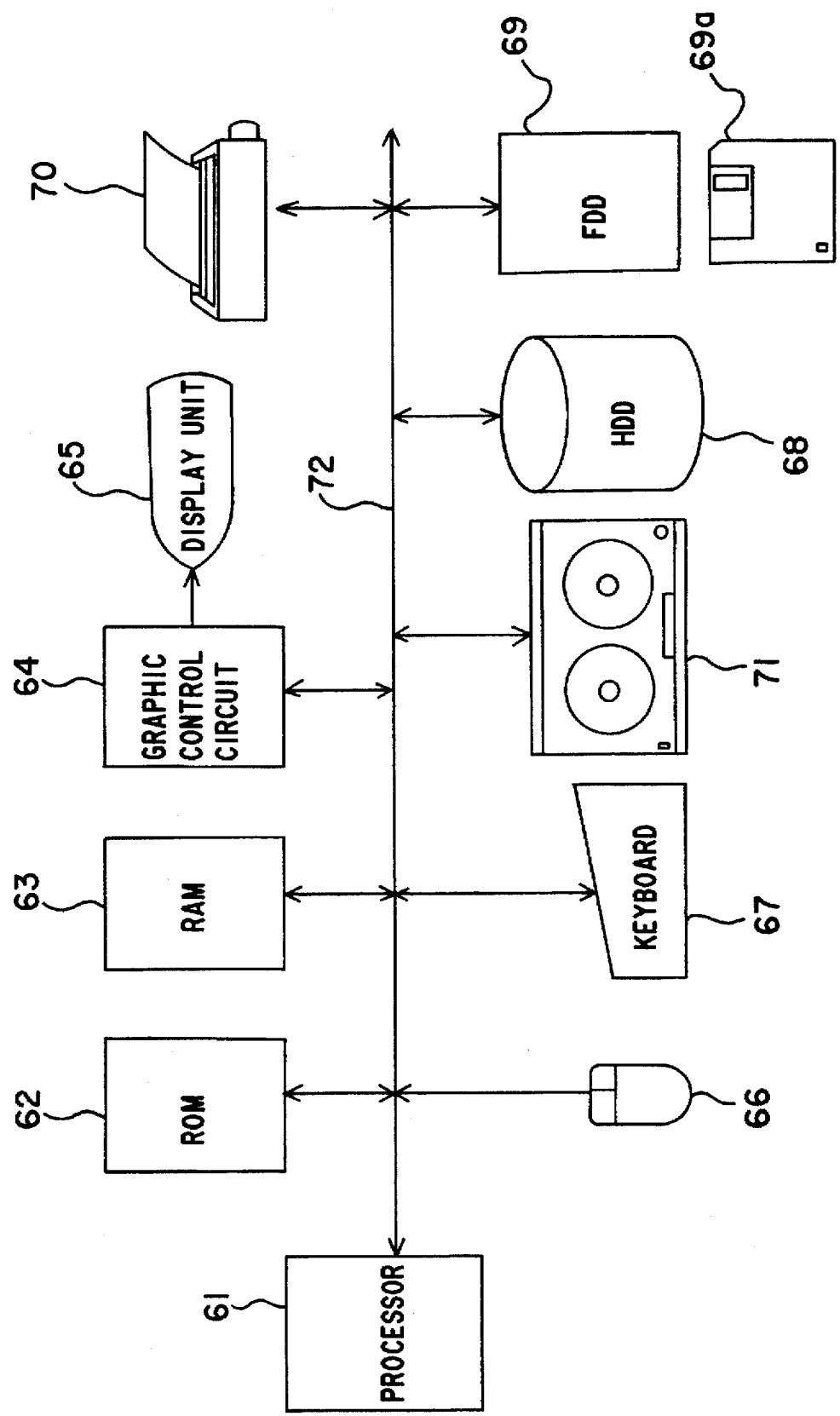
FIG. 23 is a block diagram of the hardware arrangement of a work station for implementing the apparatus for simulating an ocular optical system according to the present invention.

A hardware arrangement for carrying out the above simulation processes will briefly be described below. FIG. 23 shows in block form the hardware arrangement of a work station for implementing the apparatus for simulating an ocular optical system according to the present invention.

As shown in FIG. 23, the work station comprises a processor 61, a graphic control circuit 64, a display unit 65, a mouse 66, a keyboard 67, a hard disk drive (HDD) 68, a floppy disk drive (FDD) 69, a printer 70, and a magnetic tape device 71. These components of the work station are interconnected by a bus 72.

The processor 61 controls the work station in its entirety. The work station also has a read-only memory (ROM) 62 which stores a system program which is necessary to start the work station, and a random-access memory (RAM) as a main memory 63 for storing a simulation program for carrying out a simulation process.

The graphic control circuit 64 includes a video memory, converts retinal image data or scenery image data which have been obtained by a simulation process into a display signal, and supplies the display signal to the display unit 65 to display a corresponding image thereon. The mouse 66 is a pointing device for controlling a mouse displayed on the display unit 65 and selecting various icons and menus.

The hard disk drive 68 stores the system program and the simulation program, which are loaded into the main memory 63 when the work station is switched on. The hard disk drive 68 temporarily stores simulated data, etc.

The floppy disk drive 69 reads data such as original image data from a floppy disk 69a or saves such data on the floppy disk 69a.

The printer 70 is used to print PSFs, retinal image data, and scenery image data.

The magnetic tape device 71 is used to save simulated data on a magnetic tape.

A high-performance personal computer or a general-purpose computer may be used instead of the work station.

The foregoing is considered as illustrative only of the principles of the present invention. Further, since numerous modifications and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. An apparatus for simulating an ocular optical system to simulate a retinal image produced by a human eye through an optical lens, comprising:

point-spread-function calculating means for calculating a point spread function based on optical system data including data of a light source display screen disposed in a given position, data of the optical lens, and data of the human eye which includes a cornea, a pupil, and a retina; and retinal image calculating means for calculating a retinal image based on image data disposed in a given position and said point spread function.

2. An apparatus for simulating an ocular optical system to simulate a retinal image produced by a human eye through an optical lens, comprising:

point-spread-function calculating means for calculating point spread functions with respect to a plurality of wavelengths based on optical system data including data of a light source display screen disposed in a given position, and optical system data of the optical lens and the human eye with respect to said wavelengths; and retinal image calculating means for calculating monochromatic retinal images with respect to said wavelengths based on original image data and said point spread functions with respect to said wavelengths.

3. An apparatus for simulating an ocular optical system to simulate a retinal image produced by a human eye through an optical lens, comprising:

image dividing means for dividing original image data disposed in a given position into monochromatic image data with respect to a plurality of wavelengths;

point-spread-function calculating means for calculating point spread functions with respect to said wavelengths based on optical system data including data of a light source display screen disposed in a given position, and optical system data of the optical lens and the human eye with respect to said wavelengths;

retinal image calculating means for calculating monochromatic retinal images with respect to said wavelengths based on said monochromatic image data and said point spread functions with respect to said wavelengths; and retinal image combining means for combining said monochromatic retinal images with respect to said wavelengths into a retinal image.

4. An apparatus according to claim 3, wherein said point-spread-function calculating means comprises means for calculating said point spread functions based on the optical system data with respect to an angle through which the human eye is turned, said angle being established by a parameter.

5. An apparatus according to claim 3, wherein said wavelengths comprise at least a combination of wavelengths of an e-line, an F'-line, and a C'-line or a combination of wavelengths of an d-line, an F-line, and a C-line.

6. An apparatus according to claim 3, further comprising display control means for displaying said retinal image on a display unit.

7. An apparatus according to claim 6, wherein said display control means comprises means for displaying a plurality of retinal images generated based on optical system data of a plurality of optical lenses having different Abbe numbers, simultaneously on said display unit.

8. An apparatus according to claim 3, wherein said retinal image combining means comprises means for generating said retinal image by determining intensities of red, green, and blue primaries of the monochromatic retinal images with respect to said wavelengths with color matching functions.

9. A method of simulating an ocular optical system to simulate a retinal image produced by a human eye through an optical lens, comprising the steps of:

dividing original image data disposed in a given position into monochromatic image data with respect to a plurality of wavelengths;

calculating point spread functions with respect to said wavelengths based on optical system data including data of a light source display screen disposed in a given position, and optical system data of the optical lens and the human eye with respect to said wavelengths;

calculating monochromatic retinal images with respect to said wavelengths based on said monochromatic image data and said point spread functions with respect to said wavelengths; and combining said monochromatic retinal images with respect to said wavelengths into a retinal image.

10. An apparatus for simulating an ocular optical system to simulate a retinal image produced by a human eye through an optical lens, comprising:

point-spread-function calculating means for calculating point spread functions with respect to a plurality of view dots on a light source display screen disposed in a given position, based on optical system data of the optical lens and the human eye when the human eye is turned to focus an image of the view dots on a retina of the human eye; and scenery image calculating means for calculating a scenery image in a range which can be seen when the human eye is turned, based on image data and said point spread functions with respect to said view dots.

11. An apparatus according to claim 10, further comprising display control means for displaying said scenery image on a display unit.

12. An apparatus according to claim 11, wherein said display control means comprises means for displaying a plurality of scenery images generated based on optical system data of a plurality of optical lenses having different Abbe numbers, simultaneously on said display unit.

13. An apparatus for simulating an ocular optical system to simulate a retinal image produced by a human eye through an optical lens, comprising:

point-spread-function calculating means for calculating point spread functions with respect to a plurality of view dots on a light source display screen disposed in a given position, based on optical system data of the optical lens and the human eye with respect to a plurality of wavelengths when the human eye is turned to focus an image of the view dots on a retina of the human eye;

scenery image calculating means for calculating monochromatic scenery images with respect to said wavelengths in a range which can be seen when the human eye is turned, based on original image data and said point spread functions with respect to said view dots and said wavelengths; and scenery image combining means for combining said monochromatic scenery images with respect to said wavelengths into a scenery image.

14. An apparatus for simulating an ocular optical system to simulate a retinal image produced by a human eye through an optical lens, comprising:

point-spread-function calculating means for calculating point spread functions with respect to a plurality of view dots on a light source display screen disposed in a given position, based on optical system data of the optical lens and the human eye with respect to a plurality of wavelengths when the human eye is turned to focus an image of the view dots on a retina of the human eye;

image dividing means for dividing original image data disposed in a given position into monochromatic image data with respect to said wavelengths;

scenery image calculating means for calculating monochromatic scenery images with respect to said wavelengths in a range which can be seen when the human eye is turned, based on said monochromatic image data and said point spread functions with respect to said view dots and said wavelengths; and scenery image combining means for combining said monochromatic scenery images with respect to said wavelengths into a scenery image.

15. An apparatus according to claim 14, wherein said wavelengths comprise at least a combination of wavelengths of an e-line, an F'-line, and a C'-line or a combination of wavelengths of an d-line, an F-line, and a C-line.

16. An apparatus according to claim 14, further comprising display control means for displaying said scenery image on a display unit.

17. An apparatus according to claim 14, wherein said scenery image combining means comprises means for generating said scenery image by determining intensities of red, green, and blue primaries of the monochromatic scenery images with respect to said wavelengths with color matching functions.

18. An apparatus for simulating an ocular optical system to simulate a retinal image produced by a human eye through an optical lens, comprising:

point-spread-function calculating means for calculating point spread functions based on turned-state optical system data including data of a light source display screen positioned to focus light entered through the optical lens on a retina of the human eye, data of the optical lens disposed in a path of travel of light from the light source display screen, and data of the human eye, when the human eye is turned through an optional angle; and retinal image calculating means for calculating a retinal image generated by image data displayed by the light source display screen and said point spread functions.

19. An apparatus according to claim 18, further comprising display control means for displaying said retinal image on a display unit.

20. An apparatus according to claim 18, wherein said optical lens comprises a monofocal lens or a multifocal lens.

21. An apparatus according to claim 18, wherein said optical lens comprises a monofocal spherical lens or a monofocal aspherical lens.

22. An apparatus for simulating an ocular optical system to simulate a retinal image produced by a human eye through an optical lens, comprising:

optical system data storage means for storing turned-state optical system data including data of a light source display screen positioned to focus light entered through the optical lens on a retina of the human eye, data of the optical lens disposed in a path of travel of light from the light source display screen, and data of the human eye, when the human eye is turned through an optional angle;

optical system data selecting means for selecting one of the turned-state optical system data from said optical system data storage means;

point-spread-function calculating means for calculating point spread functions based on the selected turned-state optical system data; and retinal image calculating means for calculating a retinal image generated by image data displayed by the light source display screen and said point spread functions.

23. An apparatus according to claim 22, further comprising display control means for displaying said retinal image on a display unit.

24. An apparatus for simulating an ocular optical system to simulate a retinal image produced by a human eye through an optical lens, comprising:

turned-state optical system data calculating means for calculating turned-state optical system data including data of a light source display screen positioned to focus light entered through the optical lens on a retina of the human eye, data of the optical lens disposed in a path of travel of light from the light source display screen, and data of the human eye, when the human eye is turned through an optional angle, based on reference optical system data including data of the light source display screen, data of the optical lens, and data of the human eye;

point-spread-function calculating means for calculating point spread functions based on the calculated turned-state optical system data; and retinal image calculating means for calculating a retinal image generated by image data displayed by the light source display screen and said point spread functions.

25. An apparatus according to claim 24, wherein said reference optical system data comprise optical system data produced when the human eye is not turned.

* * * * *